(12) United States Patent
Sekido et al.

(10) Patent No.: US 10,786,980 B2
(45) Date of Patent: Sep. 29, 2020

(54) LAMINATE AND PRODUCTION METHOD THEREFOR

(71) Applicant: Toray Industries, Inc., Tokyo (JP)

(72) Inventors: Yuki Sekido, Otsu (JP); Motonori Hochi, Otsu (JP); Toru Arakane, Tokyo (JP); Yoshikazu Yakake, Otsu (JP); Teruhisa Sato, Mishima (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/311,314

(22) PCT Filed: Jun. 18, 2015

(86) PCT No.: PCT/JP2015/067553
§ 371 (c)(1),
(2) Date: Nov. 15, 2016

(87) PCT Pub. No.: WO2015/194616
PCT Pub. Date: Dec. 23, 2015

(65) Prior Publication Data
US 2017/0072669 A1    Mar. 16, 2017

(30) Foreign Application Priority Data

Jun. 18, 2014 (JP) .................................. 2014-124935
Jun. 24, 2014 (JP) .................................. 2014-128864

(51) Int. Cl.
*B32B 27/36* (2006.01)
*B32B 38/10* (2006.01)
(Continued)

(52) U.S. Cl.
CPC ............ *B32B 27/36* (2013.01); *A61L 15/225* (2013.01); *A61L 15/24* (2013.01); *A61L 15/26* (2013.01);
(Continued)

(58) Field of Classification Search
CPC ........ A61L 15/225; A61L 31/00; A61L 15/16; B32B 27/36; B32B 38/10; B32B 27/12;
(Continued)

(56) References Cited

U.S. PATENT DOCUMENTS 5,010,145 A * 4/1991 Ikada ..................... D01F 6/92
                                                    525/415
5,630,972 A * 5/1997 Patnode ................. A61L 15/62
                                                    264/103
(Continued)

FOREIGN PATENT DOCUMENTS

JP    2000017164 A  *  1/2000
JP    2001-145650 A     5/2001
(Continued)

OTHER PUBLICATIONS

Espacenet Translation of JP 2000-017164 (Year: 2019).*

*Primary Examiner* — Michael Zhang
(74) *Attorney, Agent, or Firm* — DLA Piper LLP (US)

(57) ABSTRACT

A laminate has at least one polylactic acid resin-containing layer (C) with a thickness of 10-500 nm on at least one surface of a fibrous structure (B) containing a water-soluble resin (A). A production method for the laminate is characterized in that water or an aqueous solution is applied to the joining surface of the fibrous structure (B) and the polylactic acid resin-containing layer (C). The laminate exhibits excellent followability, adherence and coatability relative to flexible, curved adherends, exhibits excellent compatibility to organs such as skin and internal organs, and, because the fibrous structure (B) containing a water-soluble resin (A) can easily be removed from the polylactic acid resin-containing layer (C) by the aqueous solution, is adapted for use in materials for external use on the skin, such as wound-dressing materials, adhesion-preventing materials, and skin care products.

7 Claims, 3 Drawing Sheets

(51) Int. Cl.
| | |
|---|---|
| *B32B 5/26* | (2006.01) |
| *B32B 15/14* | (2006.01) |
| *B32B 7/12* | (2006.01) |
| *A61L 15/28* | (2006.01) |
| *A61L 15/26* | (2006.01) |
| *A61L 31/04* | (2006.01) |
| *B32B 29/02* | (2006.01) |
| *A61L 31/06* | (2006.01) |
| *B32B 7/04* | (2019.01) |
| *A61L 15/24* | (2006.01) |
| *A61L 15/22* | (2006.01) |
| *B32B 5/02* | (2006.01) |
| *B32B 9/04* | (2006.01) |
| *B32B 27/08* | (2006.01) |
| *B32B 27/12* | (2006.01) |
| *B32B 27/30* | (2006.01) |
| *B32B 37/10* | (2006.01) |
| *B32B 37/18* | (2006.01) |

(52) U.S. Cl.
CPC ............ *A61L 15/28* (2013.01); *A61L 31/041* (2013.01); *A61L 31/042* (2013.01); *A61L 31/048* (2013.01); *A61L 31/06* (2013.01); *B32B 5/022* (2013.01); *B32B 5/26* (2013.01); *B32B 7/04* (2013.01); *B32B 7/12* (2013.01); *B32B 9/045* (2013.01); *B32B 9/047* (2013.01); *B32B 15/14* (2013.01); *B32B 27/08* (2013.01); *B32B 27/12* (2013.01); *B32B 27/306* (2013.01); *B32B 29/02* (2013.01); *B32B 37/10* (2013.01); *B32B 37/182* (2013.01); *B32B 38/10* (2013.01); *B32B 2262/00* (2013.01); *B32B 2262/02* (2013.01); *B32B 2262/0223* (2013.01); *B32B 2262/04* (2013.01); *B32B 2270/00* (2013.01); *B32B 2307/412* (2013.01); *B32B 2307/7163* (2013.01); *B32B 2307/7166* (2013.01); *B32B 2307/726* (2013.01); *B32B 2307/748* (2013.01); *B32B 2405/00* (2013.01); *B32B 2437/00* (2013.01); *B32B 2535/00* (2013.01); *B32B 2555/02* (2013.01); *B32B 2556/00* (2013.01)

(58) Field of Classification Search
CPC ......... B32B 5/022; B32B 9/045; B32B 9/047; B32B 27/08; B32B 37/182; B32B 27/306; B32B 37/10; B32B 2262/02; B32B 2535/00; B32B 2262/00; B32B 2262/0223; B32B 2307/726
See application file for complete search history.

(56) References Cited

U.S. PATENT DOCUMENTS

| | | | |
|---|---|---|---|
| 8,900,351 B2 | 12/2014 | Mori et al. | |
| 2003/0100955 A1 | 5/2003 | Greenawalt et al. | |
| 2003/0195611 A1* | 10/2003 | Greenhalgh | A61F 2/07 623/1.15 |
| 2007/0172651 A1* | 7/2007 | Miyoshi | D01D 5/0038 428/373 |
| 2007/0238384 A1* | 10/2007 | Tang | A41D 31/0083 442/381 |
| 2008/0161508 A1* | 7/2008 | Matsumoto | C08L 67/04 525/450 |
| 2010/0056751 A1* | 3/2010 | Toyohara | C08G 63/08 528/354 |
| 2011/0151737 A1* | 6/2011 | Moore | D04H 3/007 442/334 |
| 2011/0259518 A1* | 10/2011 | Tojo | B32B 5/02 156/308.6 |
| 2013/0122069 A1* | 5/2013 | Tojo | A61K 8/0208 424/401 |
| 2013/0142852 A1* | 6/2013 | Tojo | A61K 8/0208 424/401 |
| 2014/0356603 A1* | 12/2014 | Kumar | C08J 5/122 428/216 |
| 2015/0209243 A1* | 7/2015 | Shiroya | A61K 8/676 424/401 |
| 2015/0265030 A1* | 9/2015 | Kusukame | A45D 44/002 132/200 |
| 2015/0282595 A1* | 10/2015 | Kimura | A61Q 17/04 132/200 |
| 2016/0002422 A1* | 1/2016 | Hochi | B32B 7/02 428/216 |

FOREIGN PATENT DOCUMENTS

| | | |
|---|---|---|
| JP | 2001-192337 A | 7/2001 |
| JP | 2003-153999 A | 5/2003 |
| JP | 2003-516816 A | 5/2003 |
| JP | 2003-251749 A | 9/2003 |
| JP | 2004-065780 A | 3/2004 |
| JP | 2005-224981 A | 8/2005 |
| JP | 2014-30825 A | 2/2014 |
| JP | 2014-094214 A | 5/2014 |
| WO | 2005/094915 A1 | 10/2005 |
| WO | 2011/081162 A1 | 7/2011 |

* cited by examiner

LAMINATE AND PRODUCTION METHOD THEREFOR

TECHNICAL FIELD

This disclosure relates to a laminate having a fibrous structure containing a water-soluble resin and a polylactic acid resin-containing layer which is optimum for use in medical applications such as wound-dressing membranes or adhesion-preventing membranes, and a production method therefor.

BACKGROUND

In a surgical operation represented by abdominal surgery, plastic surgery, neurosurgery, etc., there is a problem of adhesion between organs as one of complications after the operation. This is caused from the phenomenon wherein, when normal tissues having received injury due to drying and oxidation are stitched to each other to be closed in the operation, in a process of being self-healed by healing of the wound, an adhesion phenomenon, namely, conjugation of the tissues of organs to each other which essentially must not happen, may be caused. It is said that an adhesion is caused at a high possibility in a surgical operation, the adhesion may lead to pain or a complication causing a serious symptom such as ileus or sterility.

It is difficult to treat an adhesion once caused, with medicine. Further, ileus due to an adhesion may be caused even after several years are passed after operation. It is considered that adhesion can be treated only by adhesion separation surgery that separates the adhesion part by conducting another surgical operation and, therefore, in a surgical operation, prevention of adhesions is extremely important.

So far, as a treatment to prevent tissue adhesion or delay of healing after operation, a method of covering an exposed organ tissue with a piece of gauze dipped in saline to prevent drying and oxidation has been employed. However, because an organ has an complicated and flexible property, the method can cause problems such as ones that a sufficient covering cannot be carried out by the gauze, the gauze becomes an obstacle relative to a doctor during the operation, and the possibility of leaving the gauze in the body is increased because much gauze is used.

From such reasons, as the materials having an effect of preventing adhesion or preventing delay of healing, a method of using a silicone, "Teflon" (registered trademark), a polyurethane, an oxycellulose and the like as an adhesion-preventing membrane has been employed to physically separate origin tissues, but, because these materials are non-bioabsorbable materials, they are left on the surface of the biological tissue, and not only do they delay repair of the tissue, but also they become origins causing infection and inflammation.

In recent years, to solve such problems, adhesion-preventing materials using gelatin or collagen which can expect bioabsorbability are reported (for example, JP-A-2004-065780 and JP-A-2001-192337). When gelatin or collagen is used, however, there is a problem where it is difficult to remove a telopeptide part having an antigenicity and, further, because there is a risk of an animal-derived infectious disease such as prion contamination, it is considered that it is better to avoid use to an organism. Moreover, it is considered that there are many cases where a crosslinking agent added to obtain strength and control degradability is not preferred for use in an organism.

On the other hand, in a natural polymer, there is such a problem that it is low in strength though it is high in affinity with skin. Therefore, in a natural polymer, it has been necessary to ensure strength by a material crosslinked with a crosslinking agent or by use of a reinforcement material or by wrapping with a gauze. However, when a reinforcement material is used, because there are many cases where the structure becomes complicated, it is not practical.

Further, an adhesion-preventing material using a polysaccharide such as trehalose which is low in risk of infectious disease is also reported (for example, JP-A-2003-153999). However, in a material using a polysaccharide, it is poor in strength, and there is a problem that suturing is difficult because of lack of strength. Further, even if suturing is possible, it is difficult to maintain a sutured state for a certain period of time.

Further, although an adhesion-preventing material using a hyaluronic acid is also reported (for example, WO 2005/094915 A1), because of its poor adherence to an organ, the membrane and the organ are liable to be shifted from each other, and whereby an adhesion may be caused and, therefore, it does not always have a satisfactory performance. Further, there is a problem that it is high in manufacturing cost because it is difficult to mass produce. To strongly adhere the adhesion-preventing membrane to the organ and the like, although there are methods of using blood products and using chemical substances, these methods include a problem that high-quality management in viewpoints of hygiene and safety is required and it is difficult to be handled.

Thus, although there are many reports relating to materials to prevent tissue adhesion, a material having a satisfactory performance as an adhesion-preventing material has not been obtained. Namely, a material, being hard to cause the above-described problems and capable of preventing adhesion until a tissue is recovered and maintaining a strength until the tissue is recovered, is required.

On the other hand, with respect to a production method of a laminate having a fibrous structure (B) containing a water-soluble resin and a polylactic acid resin-containing layer (C) which is optimum to use for medical applications, although it is considered to apply the following conventional general production methods, there are the following problems in the conventional methods.

For example, as a production method of a laminate, there is a dry laminating method of manufacturing a polylactic acid resin-containing layer (C) and a fibrous structure (B) separately and laminating the polylactic acid resin-containing layer (C) and the fibrous structure (B) using an adhesive (for example, JP-A-2005-224981). However, because an organic solvent is used, a special waste liquid facility and exhaust equipment are required from the viewpoint of environmental load, and use of a protection device such as a gas mask is required to prevent health damage to an operator and the like and, thus, many considerations are required in production activities. In addition, an organic solvent, which is low in contribution to performance of a final product, is used, at the production stage the solvent is evaporated and disposed outside the product, which adversely affects cost.

Further, as a production method not using an organic solvent with respect to a production method of a laminate, there is an extrusion laminating method of delivering a molten resin onto a surface of a fibrous structure (B) produced in advance using an extruder and the like and, thereafter, solidifying it (for example, JP-A-2003-251749). However, there is a quality problem causing an appearance defect such as one that the fibrous structure collapses by heating and press contacting and the thickness is reduced. Moreover, when a resin low in thermal decomposition temperature is supplied to an extruder, there are problems such as deterioration of the resin is caused, a large amount of thermal energy is required for melting the resin and, further, the environment for operation becomes a high temperature or the like.

Further, as a production method that can reduce energy used to melt a resin with respect to a production method of a laminate, there is a thermally laminating method to thermally fuse and press contact a part of the contact portion of a polylactic acid resin-containing layer (C) and a fibrous structure (B) (for example, JP-A-2014-30825). However, there is a quality problem causing an appearance defect such as one that the fibrous structure collapses by heating and press contacting and the thickness is reduced. In particular, when the polylactic acid resin-containing layer (C) is a thin membrane, there is a quality problem that, if heat is too applied, it melts and the polylactic acid resin-containing layer (C) itself collapses. Further, there is a problem that a large amount of thermal energy is required to heat the polylactic acid resin-containing layer (C) and the fibrous structure (B), a heat-transfer body such as a metal roller or plate used heating is required to be elevated in temperature in advance before production, and the working efficiency thereof is poor by reason of excessive time.

Further, as a production method that can reduce a load due to heat or pressure applied to a fibrous structure (B) with respect to a production method of a laminate, there is a method of providing an adhesive layer between the fibrous structure (B) and a polylactic acid resin-containing layer (C) (for example, JP-A-2001-145650). However, there is a problem that the bending ability of the laminate is poor as compared to a single layer of the fibrous structure (B) because the thickness of the adhesive layer is great, thereby causing damage to flexibility, or a problem that the adherence becomes poor on account of a small contact area of the adhesive layer with the fibrous structure (B).

Furthermore, as a production method that does not provide an adhesive layer with respect to a production method of a laminate, there is a method of needle punching to physically fix a fibrous structure (B) and a polylactic acid resin-containing layer (C) by stacking the fibrous structure (B) and the polylactic acid resin-containing layer (C) which are manufactured separately from each other, and pressing a needle to a plurality of places from a surface of the fibrous structure (B) or the polylactic acid resin-containing layer (C) to entangle the fibrous structure (B) and the polylactic acid resin-containing layer (C) to each other (for example, JP-A-2014-94214). However, because it is necessary to perforate the polylactic acid resin-containing layer (C), it cannot be used when it is required that passage of a liquid, a gas, or the like is interrupted by the layer and, further, when the polylactic acid resin-containing layer (C) is thin, there is a problem that it is greatly broken when the needle is penetrated therethrough.

In consideration of the background of such conventional technologies, it could be helpful to provide a laminate laminated with a fibrous structure (B) containing a water-soluble resin and a polylactic acid resin-containing layer (C) adapted for use in medical applications such as wound-dressing membranes or adhesion-preventing membranes, which is excellent in biocompatibility and easy in handling ability, and which is excellent in economic efficiency.

Further, it could be helpful to provide a method for producing a laminate excellent in working efficiency and productivity when the above-described fibrous structure (B) containing a water-soluble resin and polylactic acid resin-containing layer (C) are laminated to each other, and low in environmental load and, in addition, that can produce a laminate excellent in appearance without breaking the polylactic acid resin-containing layer (C), in particular, that can enhance the appearance quality (wrinkle, unevenness in lamination or the like) even when the polylactic acid resin-containing layer (C) is thin.

SUMMARY

We thus provide:

(1) A laminate having at least one polylactic acid resin-containing layer (C) with a thickness of 10 nm-500 nm on at least one surface of a fibrous structure (B) containing a water-soluble resin (A).

(2) The laminate according to (1), wherein at least one layer (D) containing a water-soluble resin (E) with a thickness of 0.01 μm-15 μm is provided between the fibrous structure (B) containing a water-soluble resin (A) and the polylactic acid resin-containing layer (C).

(3) The laminate according to (1) or (2), wherein a time required from a timing at that water is applied to one surface of the fibrous structure (B) containing a water-soluble resin (A) until a timing at that the water reaches another surface of the fibrous structure (B) is a range of 10 seconds to 5 minutes.

(4) The laminate according to any one of (1) to (3), wherein the water-soluble resin (A) contains a polyvinyl alcohol and/or a pullulan.

(5) The laminate according to (2), wherein the water-soluble resin (E) contains a polyvinyl alcohol and/or a pullulan.

(6) The laminate according to any one of (1) to (5), wherein an areal weight of the fibrous structure (B) containing a water-soluble resin (A) is in a range of 1 $g/m^2$ to 1,000 $g/m^2$.

(7) The laminate according to any one of (1) to (6), wherein a thickness of the fibrous structure (B) containing a water-soluble resin (A) is in a range of 0.1 μm to 5,000 μm.

(8) The laminate according to any one of (1) to (7), wherein the polylactic acid resin is one with an amount of poly-D-lactic acid in a range of 4 mol % to 50 mol %.

Further, a method of producing a laminate has the following constitution:

(9) A method of producing a laminate comprising the step of, when a fibrous structure (B) containing a water-soluble resin (A) and a polylactic acid resin-containing layer (C) are laminated, applying water or an aqueous solution to a joining surface of the fibrous structure (B) and the polylactic acid resin-containing layer (C).

(10) The method of producing a laminate according to (9), wherein the fibrous structure (B) containing a water-soluble resin (A) and the polylactic acid resin-containing layer (C) are laminated at a condition being fixed onto respective flat plates.

(11) The method of producing a laminate according to (9), wherein the fibrous structure (B) containing a water-soluble resin (A) and the polylactic acid resin-containing layer (C) are laminated by being nipped between two rollers.

The laminate is a laminate laminated with at least one polylactic acid resin-containing layer (C) on at least one surface of a fibrous structure (B) containing a water-soluble resin (A) since it is flexible and excellent in handling ability and the fibrous structure (B) containing a water-soluble resin (A) of a thick layer can be easily removed from the polylactic acid resin-containing layer (C) of a thin layer by an aqueous solution when it is applied to an adherend, it is excellent in followability, adherence and coatability relative to the adherend having a curved surface and, further, if a biodegradable component is selected, it exhibits excellent compatibility to organs such as skin and internal organs, and it is adapted for use in materials for external use on the skin such as wound-dressing materials, adhesion-preventing materials, and skin care products.

Further, by providing at least one layer (D) containing a water-soluble resin (E) between the fibrous structure (B) containing a water-soluble resin (A) and the polylactic acid resin-containing layer (C), the adhesive property between the polylactic acid resin-containing layer (C) and the fibrous structure (B) containing the water-soluble resin (A) can be improved, the laminate can be more stabilized relative to stress from outside, and handling ability as a laminate can be improved.

Further, since materials that form the laminate are a polylactic acid resin and a water-soluble resin, the laminate can be inexpensively mass produced, and it is excellent in economic efficiency.

Moreover, since the polylactic acid resin-containing layer (C) after being removed with the fibrous structure (B) containing a water-soluble resin (A) by water or an aqueous solution is transparent, a surface stuck with it is not conspicuous and, therefore, it can be applied not only to surgical operations, but also to sticking to skin, and also to use as a plaster.

Furthermore, loading or sustained release of various chemicals is possible using the polylactic acid resin-containing layer (C) as a base material, and the laminate can be used also as a drug delivery system.

Further, in the method of producing a laminate, when the above-described fibrous structure (B) containing a water-soluble resin (A) and the polylactic acid resin-containing layer (C) are laminated, water or an aqueous solution is applied to a joining surface of the fibrous structure (B) and the polylactic acid resin-containing layer (C) (as a method of applying water or the aqueous solution, for example, there are methods such as spraying, coating and dropping, and it is preferred to apply it by spraying.), thereby laminating the fibrous structure (B) containing a water-soluble resin (A) and the polylactic acid resin-containing layer (C) and, therefore, as compared to conventional production methods, it is extremely simple and excellent in working efficiency and, further, it is a production method small in environmental load.

By providing at least one layer (D) containing a water-soluble resin (E) between the fibrous structure (B) containing a water-soluble resin (A) and the polylactic acid resin-containing layer (C), as compared to conventional production methods, lamination of the fibrous structure (B) containing a water-soluble resin (A) and the polylactic acid resin-containing layer (C) becomes easy.

Further, when the thickness of the layer (D) containing a water-soluble resin (E) is 0.01 µm-15 µm, as compared to conventional production methods, the appearance quality (unevenness in lamination or the like) can be improved, the yield is enhanced and the cost competitiveness is excellent and, therefore, such a condition is preferred. When the thickness of the layer (D) containing a water-soluble resin (E) is less than 0.01 µm, there is a possibility that the appearance quality (unevenness in lamination or the like) is poor, and when more than 15 µm, there is a possibility that the cost competitiveness is poor.

As the lamination method in the method of producing a laminate, by laminating the fibrous structure (B) containing a water-soluble resin (A) and the polylactic acid resin-containing layer (C) at a condition being fixed onto respective separate flat plates, or by laminating the fibrous structure (B) containing a water-soluble resin (A) and the polylactic acid resin-containing layer (C) by being nipped between two or more rollers, a laminate further excellent in appearance quality and cost competitiveness can be obtained and, therefore, such a method is preferred.

In addition, by using an aqueous solution containing a water-soluble resin for spraying, the shape of the liquid drops, after the aqueous solution is sprayed from a sprayer until it reaches the surfaces of the fibrous structure (B) containing a water-soluble resin (A) and/or the polylactic acid resin-containing layer (C) and/or the layer (D) containing a water-soluble resin (E), can be stabilized, and a laminate excellent in appearance quality can be obtained and, therefore, such a condition is preferred.

Such a method of producing a laminate is optimal, in particular, for production of medical products such as wound-dressing materials or adhesion-preventing materials and materials for external use on the skin such as skin care products, and further, also suitable for production of hygiene products and the like such as surgical gowns, antibacterial mats, poultices, stupes, artificial skins, diapers, sanitary items, gauze, first-aid adhesive tapes, cleaning supplies and masks.

EXPLANATION OF SYMBOLS

Figure 1:
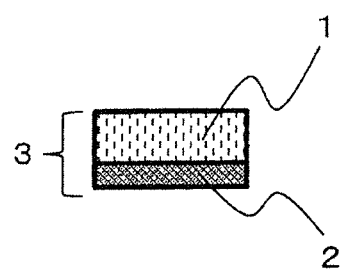
FIG. 1 is a schematic diagram of a section showing an example of a laminate.

1 fibrous structure (B) containing water-soluble resin (A)
2 polylactic acid resin-containing layer (C)
3 laminate
4 pressing jig
5 cylindrical vessel
6 adherend
11 upper roller
12 lower roller
13 rotational direction
14 PET-1

DETAILED DESCRIPTION

Hereinafter, our laminates and methods will be explained in detail together with the examples. A "film" means a structural material having a two-dimensional extension, for example, as one including a sheet, a plate, a discontinuous membrane or the like.

Polylactic Acid Resin

The weight average molecular weight of the polylactic acid resin is preferably 30,000 or more, more preferably 50,000 or more, further preferably 80,000 to 400,000, and more preferably 100,000 to 500,000. The weight average molecular weight means a molecular weight determined with a chloroform solvent by gel permeation chromatography (GPC), and calculated by conversion method with polymethyl methacrylate (PMMA). By controlling the weight average molecular weight of the polylactic acid resin to be 30,000 or more, the mechanical properties of the polylactic acid resin-containing layer (C), which contains such a polylactic acid resin, can be controlled to be excellent.

The polylactic acid resin may be mixed with a homo-polylactic acid resin having a crystallinity and an amorphous homo-polylactic acid resin for the purpose of improving the solubility into a solvent at the time of preparing a coating liquid for a coating layer. In this case, the rate of the amorphous homo-polylactic acid resin may be decided within a range which does not damage the desired effects. Further, when a relatively high thermal resistance is desired to be provided to the polylactic acid resin-containing layer (C), at least one of the polylactic acid resins being used preferably includes a polylactic acid resin having an optical purity of 95% or more.

It is preferred that the main component of the polylactic acid resin is poly-L-lactic acid (L body) and/or poly-D-lactic acid (D body). The main component means that the content of the components originating from lactic acid is 70 mol % or more and 100 mol % or less relative to 100 mol % of all monomer components forming the polylactic acid resin, and a homo-polylactic acid resin substantially composed of only poly-L-lactic acid and/or poly-D-lactic acid is preferably used.

Further, the amount of poly-D-lactic acid of the polylactic acid resin is preferably 4 mol % to 50 mol %, and more preferably 6 mol % to 13 mol %. If the amount of poly-D-lactic acid is less than 4 mol %, the solubility into an organic solvent reduces and there is a possibility that it becomes difficult to make a coating material, and if more than 50 mol %, there is a possibility that it is hardly metabolized although there is an individual variation.

The polylactic acid resin may be a copolymerized polylactic acid resin copolymerized with another monomer component having an ester forming function other than L-lactic acid and D-lactic acid. As a monomer component capable of being copolymerized, a hydroxycarboxylic acid such as glycolic acid, 3-hydroxybutyric acid, 4-hydroxybutyric acid, 4-hydroxyvaleric acid, and 6-hydroxy-caproic acid, and in addition, compounds containing a plurality of hydroxyl groups in a molecule such as ethylene glycol, propylene glycol, butane diol, neopentyl glycol, polyethylene glycol, glycerin, or pentaerythritol, or derivatives thereof, and compounds containing a plurality of carboxylic groups in a molecule such as succinic acid, adipic acid, sebacic acid, fumaric acid, terephthalic acid, isophthalic acid, 2,6-naphthalene dicarboxylic acid, 5-sodium sulfoisophthalic acid, or 5-tetrabutylphosphonium sulfoisophthalic acid, or derivatives thereof, can be exemplified. Among the above-described copolymerized components, it is preferred to select a component having a biodegradability depending upon uses. It is preferred that these copolymerized components are contained at 40 mol % or less relative to 100 mol % of all monomer components forming the polylactic acid resin.

As the method of producing a polylactic acid resin, though the details will be described later, a direct copolymerization from a lactic acid, a ring-opening copolymerization via a lactide or the like, can be raised.

From the viewpoint of suppressing reduction of strength due to hydrolysis, thereby providing a good durability (a long-term preservation property), the concentration of carboxylic end groups in the polylactic acid resin is preferably 30 equivalents/$10^3$ kg or less, more preferably 20 equivalents/$10^3$ kg or less, and further preferably 10 equivalents/$10^3$ kg or less. If the concentration of carboxylic end groups in the polylactic acid resin is 30 equivalents/$10^3$ kg or less, because the concentration of carboxylic end groups, which also cause autocatalysis for hydrolysis, is sufficiently low, a practically good durability can be provided, and such a condition is preferred. The lower limit of the concentration of carboxylic end groups in the polylactic acid resin is not particularly restricted, and there is no problem even if it is as close to 0 equivalent as possible.

As the method of controlling the concentration of carboxylic end groups in the polylactic acid resin at a condition of 30 equivalents/$10^3$ kg or less, for example, a method of controlling it by the catalyst or thermal history at the time of synthesis of the polylactic acid resin, a method of reducing the thermal history by lowering the processing temperature or shortening the heating time for forming it in a layered shape, a method of closing the ends of the carboxylic groups using a reaction type compound or the like can be exemplified.

In the method of closing the ends of the carboxylic groups using a reaction type compound, it is preferred that at least a part of the ends of the carboxylic groups in the polylactic acid resin are closed, and it is more preferred that all the ends are closed. As the reaction type compound, for example, condensation reaction type compounds such as aliphatic alcohols and amide compounds or additional reaction type compounds such as carbodiimide compounds, epoxy compounds and oxazoline compounds can be exemplified, and additional reaction type compounds are preferred from the viewpoint that excessive by-products are hardly generated at the time of reaction, and in particular, carbodiimide compounds are preferred from the viewpoint of reaction efficiency.

In the polylactic acid resin-containing layer (C), for the purpose of improving the mechanical strength, an impact resistance improving agent may be contained in an amount of 2 mass % to 20 mass % relative to 100 mass % of the whole of the polylactic acid resin-containing layer (C). Preferably, it is 2.5 mass % to 15 mass %. As the content of the impact resistance improving agent increases, the improvement effect of the impact resistance increases, but, there is a possibility that a great improvement of mechanical properties cannot be achieved even if it is contained at a content over 20 mass %.

As the impact resistance improving agent used to improve the impact resistance, aliphatic polyesters or aliphatic aromatic polyesters other than the polylactic acid resin are preferred from the viewpoint that they have a good dispersibility in the polylactic acid resin and a higher effect can be obtained by a small amount thereof.

The aliphatic polyesters or aliphatic aromatic polyesters other than the polylactic acid resin are not particularly limited, and concretely, a polyglycolic acid, a poly(3-hydroxybutyric acid), a poly(4-hydroxybutyric acid), a poly(4-hydroxyvaleric acid), a poly(3-hydroxyhexanoic acid) or a polycaprolactone, a polyethylene adipate, a polyethylene succinate, a polybutylene succinate, a polybutylene succinate adipate or the like can be exemplified.

Furthermore, to improve the mechanical properties and maintain the biodegradability, a polybutylene succinate-based resin, which is an aliphatic polyester other than the polylactic acid resin, is preferably used. More preferably, a polybutylene succinate or a polybutylene succinate adipate, which is great in the effect of improving mechanical properties and excellent in compatibility with the polylactic acid resin, is used.

The weight average molecular weight of the polybutylene succinate-based resin is preferably 100,000 to 300,000. The polybutylene succinate-based resin is prepared by polycondensation of 1,4-butane diol and succinic acid.

The polylactic acid resin can be prepared, for example, by the following method. As the raw material, a lactic acid component of L-lactic acid or D-lactic acid and the aforementioned hydroxycarboxylic acid other than the lactic acid component can be used together. Further, cyclic ester intermediates of the hydroxycarboxylic acid, for example, such as lactide or glycolide, can also be used as the raw material. Furthermore, dicarboxylic acids or glycols can also be used.

The polylactic acid resin can be prepared by a method of directly dehydration condensing the above-described raw material or a method of ring-opening polymerizing the above-described cyclic ester intermediate. For example, when it is prepared by the direct dehydration condensation, a polymer having a high molecular weight can be prepared by polymerization by a method of serving the lactic acid or the lactic acid and the hydroxycarboxylic acid to azeotropic dehydration condensation preferably under the presence of an organic solvent, in particular, a phenylether-based solvent, preferably, by removing water from the solvent distillated by the azeotrope and returning the solvent controlled at a substantially dehydrated condition to the reaction system.

Further, it is also known that a polymer having a high molecular weight can be prepared also by ring-opening polymerizing a cyclic ester intermediate such as lactide under a pressure-reduced condition, using a catalyst such as octyl tin. At that time, a polymer small in amount of lactide can be obtained by employing a method of adjusting the condition to remove the moisture component and the low-molecular compounds in the organic solvent at the time of heat reflux, a method of suppressing a depolymerization by deactivating the catalyst after the polymerization, a method of heat treating the prepared polymer and the like.

The thickness of the polylactic acid resin-containing layer (C) is controlled to 10 nm to 500 nm from the viewpoint of the followability in shape to an adherend, and it is preferably 10 nm to 200 nm. If less than 10 nm, there is a possibility that it becomes difficult to maintain the shape, and if more than 500 nm, there is a possibility that wrinkles are generated when stuck to an adherend.

Various kinds of additives may be contained in an amount of 30 mass % or less relative to 100 mass % of the whole of the polylactic acid resin-containing layer (C) as long as the content does not damage the desired effects. As the various kinds of additives, an antioxidant, a weather resistance agent, a thermal stabilizer, a lubricant, a nucleating agent, a ultraviolet absorber, a colorant and the like can be used. The lower limit of the content of the additive is not particularly restricted, and there is no problem even if it is 0 mass % relative to 100 mass % of the whole of the polylactic acid resin-containing layer (C). Further, inorganic or organic particles may be contained in an amount of 20 mass % or less relative to 100 mass % of the whole of the polylactic acid resin-containing layer (C) as long as the content does not damage transparency. For example, calcium carbonate, titanium oxide, silicon oxide, calcium fluoride, lithium fluoride, alumina, barium sulfate, zirconia, calcium phosphate, cross-linked polystyrene-based particles or metal nanoparticles and the like can be used. The lower limit of the content of the inorganic or organic particles is not particularly restricted, and there is no problem even if it is 0 mass % relative to 100 mass % of the whole of the polylactic acid resin-containing layer (C).

Further, a bioabsorbable material layer comprising gelatin, collagen, hyaluronic acid, chitosan, synthetic polypeptide or the like may be further formed on at least one surface of the polylactic acid resin-containing layer (C) within a range which does not damage the desired effects.

Water-soluble Resin (A), Water-soluble Resin (E)

The water-soluble resin (A) and water-soluble resin (E) are polymers soluble in an aqueous solution such as water, hot water, saline or glucose solution. Concretely, a polyvinyl alcohol or a copolymer thereof, polysaccharides such as a dextran, an agarose, a pullulan, a chitosan, a mannan, a carrageenan, an alginate, a starch group (oxidized starch, etherified starch, dextrin and the like), an amylose, an amylopectin, a pectin, a lentinan, a hyaluronic acid, a hylan, a cellulose derivative (methyl cellulose, ethyl cellulose, carboxymethyl cellulose, carboxyethyl cellulose, hydoxyethyl cellulose, hydoxypropyl cellulose and the like) and the like, polypeptides such as a gelatin, a collagen, an elastin, an albumin, a hemoglobin, a transferrin, a globulin, a fibrin, a fibrinogen, a keratin sulphate and the like, copolymerized polyesters having a polar group such as a polyvinyl pyrrolidone, a sulfoisophthalic acid and the like, vinyl-based polymers such as a polyhydroxyethyl methacrylate or a copolymer thereof, acryl-based polymers, urethane-based polymers, ether-based polymers and the like, can be preferably exemplified. Further, polymers modifying these various polymers with a functional group such as a carboxylic group, an amino group, a methylol group and the like can also be preferably used. In particular, a polyvinyl alcohol and a pullulan are preferred from the viewpoint of production cost, availability and hygiene.

Polyvinyl alcohol is a saponificate of polyvinyl acetate, and the degree of saponification thereof is preferably 80 to 99.9 mol %, and more preferably 85 mol % to 98 mol %. When the degree of saponification of polyvinyl alcohol is more than 99.9 mol %, there is a possibility that the solubility of the obtained layer (D) containing a water-soluble resin (E) into water is reduced, but it can be used to the water-soluble resin (A) or the water-soluble resin (E) depending upon the purpose such as adjustment of the time of dissolution of the fibrous structure (B). The polyvinyl alcohol includes a polyvinyl alcohol copolymer. As the polyvinyl alcohol copolymer, the units of vinyl alcohol thereof are preferably 80 mol % to 98 mol %, and more preferably 85 mol % to 98 mol %.

The degree of saponification means a rate (mol %) of the mol number of the vinyl alcohol units relative to the total mol number of the structural units capable of being converted into vinyl alcohol units by saponification (typically, vinyl ester units) and the vinyl alcohol units contained in the polyvinyl alcohol or the copolymer thereof. The degree of saponification can be determined based on JIS K6726:1994.

With respect to pullulan, because of being advantageous in the points of availability and cost, usually, a pullulan, which is produced by cultivating an yeast such as genus oreobacidium in a culture medium containing starch decomposition products, can be advantageously used. For example, a pullulan sold by Hayashibara Co., Ltd. (trade name: "pullulan PI-20" and "pullulan PF-20") can be suitably used. However, it is not limited to these, and another pullulan product can also be used as long as the purpose of this disclosure does not deviate. Further, as needed, a maltotriose, made as a derivative by modification or the like such as esterification at an arbitrary substitution degree, may be employed as a repeated unit. The weight average molecular weight of a pullulan is preferred to be usually 5,000 dalton or more, preferably 10,000 dalton or more and 1,000,000 dalton or less, more preferably 50,000 dalton or more and 500,000 dalton or less. By selecting the weight average molecular weight or the molecular weight distribution of a pullulan, the layer (D) containing a water-soluble resin (E) can be controlled at a desired collapse speed. Although it is depending upon other components to be compounded, if the weight average molecular weight is less than 5,000 dalton, there is a possibility that it becomes difficult to form a sheet-like membrane, and if more than 1,000,000 dalton, there is a possibility that the dissolution speed into an aqueous solvent becomes too small.

The average degree of polymerization of a water-soluble polymer forming the water-soluble resin (A) or water-soluble resin (E) is preferably 100 to 5,000, more preferably 200 to 2,500, and further preferably 400 to 1,800. The average degree of polymerization means a number average degree of polymerization. If the average degree of polymerization is in this range, since a uniform coating layer is easily formed, the mechanical strength as the coating layer is high and it is excellent in re-solubility in an aqueous solution, such a condition is preferred. The average degree of polymerization of polyvinyl alcohol means an average degree of polymerization determined based on JIS K6726: 1994.

Two kinds or more of water-soluble polymers having different average degrees of polymerization may be mixed and used. By this, in addition to high mechanical strength and re-solubility in an aqueous solution as a coating layer, a coating layer good also in adherence with the base material film and the polylactic acid resin can be obtained and, therefore, such a condition is preferred.

It is preferred to mix and use two kinds or more of water-soluble polymers of a water-soluble polymer having a low average degree of polymerization of 100 to 800 and a water-soluble polymer having a high average degree of polymerization of 1,000 to 2,500. The water-soluble polymer having a low degree of polymerization preferably has an average degree of polymerization of 300 to 700. The water-soluble polymer having a high degree of polymerization preferably has an average degree of polymerization of 1,300 to 1,700.

Various kinds of additives may be contained in an amount of 30 mass % or less relative to 100 mass % of the whole of the water-soluble resin (A) or water-soluble resin (E) as long as the content does not damage the desired effects. The lower limit is not particularly restricted, and there is no problem even if it is 0 mass %. As the various kinds of additives, an antioxidant, a weather resistance agent, a thermal stabilizer, a lubricant, a nucleating agent, a ultraviolet absorber, a colorant or the like can be used. Further, inorganic or organic particles may be contained in an amount of 20 mass % or less as long as the content does not damage the desired effects. The lower limit is not particularly restricted, and there is no problem even if it is 0 mass %. For example, calcium carbonate, titanium oxide, silicon oxide, calcium fluoride, lithium fluoride, alumina, barium sulfate, zirconia, calcium phosphate, cross-linked polystyrene-based particles, metal nanoparticles or the like can be used.

Layer (D) Containing a Water-soluble Resin (E)

A layer (D) containing a water-soluble resin (E) may be provided between the fibrous structure (B) containing a water-soluble resin (A) and the polylactic acid resin-containing layer (C). By proving the layer (D) containing a water-soluble resin (E), the adhesive property between the fibrous structure (B) containing a water-soluble resin (A) and the polylactic acid resin-containing layer (C) is improved, the laminate is more stabilized against an external stress, and the handling ability as a laminate is improved.

The thickness of the layer (D) containing a water-soluble resin (E) is preferably 0.01 μm to 15 μm, more preferably 1 μm to 15 μm, from the viewpoints of the adhesive property to the fibrous structure (B) containing a water-soluble resin (A), the handling ability as a laminate, and the shape followability to an adherend. If it is thinner than 0.01 μm, there is a possibility that handling as a laminate becomes difficult because the adhesion with the fibrous structure (B) becomes weak, and if more than 15 μm, there is a possibility that wrinkles are generated when stuck to an adherend. or that it takes a time for being re-dissolved in water, it becomes hard to be separated from the biodegradable resin, and the adherence to an adherend is lowered.

Fibrous Structure (B) Containing a Water-soluble Resin (A)

The fibrous structure (B) includes, of course, one having a fabric form, and may be one formed from fibers having another form such as a strip-like one, a string-like one or a yarn-like one. As a fabric, a woven fabric, a knitted fabric and a nonwoven fabric are preferred, and it may be a composite material. From the viewpoint of productivity, a nonwoven fabric is preferred.

For example, in a nonwoven fabric, although the production is not particularly restricted, a fleece is formed using a dry method, a wet method, a melt blow method, a spun bond method and the like, and connection between fibers can be achieved using a chemical bond method, a thermal bond method, a needle punch method, a water complex method and the like.

The average fiber diameter of the fibers used for the fibrous structure (B) is preferably 0.001 μm to 100 μm from the viewpoints of dissolvability into water and fiber strength. By setting the average fiber diameter at 100 μm or less, sufficient flexibility and shape memory property can be provided, and therefore such a condition is preferred, and on the other hand, by setting the average fiber diameter at 0.001 μm or more, in the spinning the yarn can be stably formed, and if 0.1 μm or more, the stability at the time of spinning can be enhanced, and therefore such a condition is preferred.

Formation of the fiber used for the fibrous structure (B) is not particularly restricted, it may be formed from one kind of polymer, and there is no problem that it is formed from two or more kinds of polymers.

It is preferred that the areal weight of the fibrous structure (B) (part except a reinforcing layer described later) is 1 g/m² to 1,000 g/m². By controlling the above-described areal weight preferably at 10 g/m² or more, more preferably at 15 g/m² or more, formation stability and dimensional stability of the fibrous structure (B) are excellent and occurrence of unevenness in processing and breakage due to elongation at the time of being laminated with the polylactic acid resin-containing layer (C) can be suppressed and, therefore, such a condition is preferred. On the other hand, by controlling the above-described areal weight preferably at 400 g/m² or less, more preferably at 150 g/m² or less, the handling at the time when the fibrous structure (B) is made in a form of a roll becomes easy, and further, the cushion property of the fibrous structure (B) is appropriately suppressed, and at the time of being laminated with the polylactic acid resin-containing layer (C), the pressing pressure can be appropriately maintained at the surface of the fibrous structure (B), thereby performing an efficient lamination processing and, therefore, such a condition is preferred.

It is preferred that the thickness of the fibrous structure (B) (thickness of part except a reinforcing layer described later) is 0.1 μm to 5,000 μm. By controlling the above-described thickness preferably at 50 μm or more, more preferably at 100 μm or more, formation stability and dimensional stability of the fibrous structure (B) are excellent and occurrence of unevenness in processing and breakage due to elongation at the time of being laminated with the polylactic acid resin-containing layer (C) can be suppressed and, therefore, such a condition is preferred. On the other hand, by controlling the above-described thickness preferably at 2,000 μm or less, more preferably at 500 μm or less, the cushion property of the fibrous structure (B) is appropriately suppressed, and at the time of being laminated with the polylactic acid resin-containing layer (C), the pressing pressure can be appropriately maintained at the surface of the fibrous structure (B), thereby performing an efficient lamination processing and, therefore, such a condition is preferred.

The fibrous structure (B) contains a water-soluble resin. This is because by containing a water-soluble resin, as described later, the fibrous structure (B) can be easily dissolved with an aqueous solution such as water after being stuck to an adherend. The water-soluble resin (A) is as being aforementioned.

Concretely, with respect to the fibrous structure (B), it is preferred that the time required from a timing at that water (about 0.04 ml) is applied to one surface of the fibrous structure (B) until a timing at that the water reaches another surface of the fibrous structure (B) is a range of 10 seconds to 5 minutes. "The water reaches another surface" means a condition where the fibers of another surface of the fibrous structure (B) are dissolved so that the form of the fibers cannot be maintained. If 10 seconds or more, since the handling under presence of moisture, blood or the like can be facilitated, such a condition is preferred. In case of being used as a supporting material of an adhesion-preventing material, because a certain time is required until being stuck to a tissue, the time is preferably 30 seconds or more, particularly preferably 1 minute or more. On the other hand, if 5 minutes or less, since it can be quickly removed after being stuck to a tissue, such a condition is preferred. Although it is achieved to provide a water proof property for a long time by a method of making a layer comprising a water-insoluble polymer compound such as an outermost layer at a high areal weight or at a high density, or the like, in this case, since the feeling tends to become hard, the time is preferably 3 minutes or less, and particularly preferably 2 minutes or less.

Further, in the fibrous structure (B), for the purpose of improving the formation stability and the dimensional stability of the fibrous structure (B), a structure may be employed wherein a reinforcing layer is provided to a surface of the fibrous structure (B) opposite to the joining surface between the fibrous structure (B) and the polylactic acid resin-containing layer (C). As the reinforcing layer, can be employed a woven fabric, a knitted fabric, a nonwoven fabric (including a paper), a plastic film, a metal thin film or the like.

A treatment such as pressing may be performed to the fibrous structure (B). The press treatment may be performed at any time between processes from a process for obtaining a nonwoven fabric to a process after joining with the polylactic acid resin-containing layer (C). A heat pressing is preferably employed to enhance the setting property at the time of pressing.

Base Material

A base material in the item of a method of producing a laminate described later will be explained. A base material is used as a base material to form the layer (D) containing a water-soluble resin (E) and the polylactic acid resin-containing layer (C), or as a base material to form a single layer of the polylactic acid resin-containing layer (C).

The base material is preferably a film comprising a polymer material. As the material of a base material film, for example, exemplified are a polyolefin such as polyethylene and polypropylene, a polyester such as polyethylene terephthalate, polybutylene terephthalate and polyethylene-2,6-naphthalate, a polyamide such as nylon 6 and nylon 12, polyvinyl chloride, ethylene-vinyl acetate copolymer or a saponificate thereof, polystyrene, polycarbonate, polysulfone, polyphenylene oxide, polyphenylene sulfide, aromatic polyamide, polyimide, polyamideimide, cellulose, cellulose acetate, polyvinylidene chloride, polyacrylonitrile, polyvinyl alcohol, and copolymers thereof. From the viewpoint of ensuring an adherence with the layer (D) containing a water-soluble resin (E) and the polylactic acid resin-containing layer (C), and a uniform thickness as a film to be laminated, as the material of a base material film, a polyester such as polyethylene terephthalate, or a polyolefin such as polypropylene, is preferred. Because the wetting tension at surface is high, a polyester such as polyethylene terephthalate is particularly preferred.

It is more preferred to perform a surface treatment such as a corona discharge treatment, a flame treatment, a plasma treatment or a ultraviolet irradiation treatment, to the base material film before forming the layer (D) containing a water-soluble resin (E) or the polylactic acid resin-containing layer (C) as a coating layer.

Although the base material film may be any of a non-oriented film, a uniaxially oriented film and a biaxially oriented film, a biaxially oriented film is preferred from the viewpoint of dimensional stability and mechanical properties.

Further, various kinds of additives may be contained in the base material film. For example, an antioxidant, a weather resistance agent, a thermal stabilizer, a lubricant, a nucleating agent, a ultraviolet absorber, a colorant or the like can be contained. Further, inorganic or organic particles may be contained at a content which does not remarkably damage the surface smoothness. For example, talc, kaolinite, calcium carbonate, titanium oxide, silicon oxide, calcium fluoride, lithium fluoride, alumina, barium sulfate, zirconia, mica, calcium phosphate, cross-linked polystyrene-based particles or the like can be contained.

The average particle diameter of the above-described particles is preferably 0.001 μm to 10 μm, and more preferably 0.003 μm to 5 μm. The average particle diameter means a particle diameter determined by taking a photograph at a magnification of 10,000 times to 100,000 times using a transmission-type electron microscope or the like and calculating in a manner of number average.

Furthermore, these base material films are preferably transparent. The total light transmittance of a base material film is preferably 40% or more, further preferably 60% or more, and there is no problem even if the upper limit is close to 100% as much as possible. The haze of a base material film is preferably 20% or less, and more preferably 15% or less. If the haze is more than 20%, there is a possibility that inspection by an optical inspection machine with respect to impurities contained in the laminated layer (D) containing a water-soluble resin (E) and polylactic acid resin-containing layer (C) becomes difficult. The lower limit of the haze is not particularly restricted, and there is no problem even if it is as close to 0% as possible.

Although the thickness of the base material film is not particularly restricted, it is preferably 2 μm to 1,000 μm, and more preferably 10 μm to 500 μm from the viewpoint of economy.

Production Method

Next, a typical production method of a laminate will be described.

Method of Producing a Laminate

Although the method of producing a laminate is not particularly restricted, for example, the following method can be employed:

(1) A laminated layer of the layer (D) containing a water-soluble resin (E) and the polylactic acid resin-containing layer (C), or a single layer of the polylactic acid resin-containing layer (C) is formed on a base material film which becomes a base material.

(2) The formed polylactic acid resin-containing layer (C) (or, the laminated layer of the polylactic acid resin-containing layer (C) and the layer (D) containing a water-soluble resin (E) in case where the layer (D) containing a water-soluble resin (E) is present) is delaminated from the base material film.

(3) The formed and delaminated layer and the fibrous structure (B) containing a water-soluble resin (A) are stuck and laminated to each other, and fixed to each other. At this lamination, water or an aqueous solution is provided between the formed and delaminated layer and the fibrous structure (B) (for example, provided by spraying).

Method of Making a Single Layer of a Polylactic Acid Resin-containing Layer (C)

Although the method of making a single layer of a polylactic acid resin-containing layer (C) is not particularly restricted, for example, the following methods can be considered:

(1) A method of mechanically delaminating the laminated layer of the layer (D) containing a water-soluble resin (E) and the polylactic acid resin-containing layer (C) from the base material film, and thereafter, obtaining a single layer of the polylactic acid resin-containing layer (C) by dissolving the layer (D) containing a water-soluble resin (E) into an aqueous solution, thereby removing it.

(2) A method of dipping the laminated layer of the layer (D) containing a water-soluble resin (E) and the polylactic acid resin-containing layer (C) in an aqueous solution, and dissolving the layer (D) containing a water-soluble resin (E) and removing it, thereby obtaining a single layer of the polylactic acid resin-containing layer (C). As the aqueous solution, although various aqueous solutions such as saline and glucose solution can be used, in particular, water is preferably used.

(3) A method of laminating the polylactic acid resin-containing layer (C) onto a base material film having a smooth surface, and obtaining a single layer of the polylactic acid resin-containing layer (C) by mechanically delaminating the polylactic acid resin-containing layer (C) from the base material film. However, since there is a possibility that the polylactic acid resin-containing layer (C) is thin and the processing becomes difficult, or that a defect such as a pinhole is liable to occur, if possible, it is preferably made through a condition of the laminated layer of the layer (D) containing a water-soluble resin (E) and the polylactic acid resin-containing layer (C).

Method of Making a Laminated Layer of a Polylactic Acid Resin-containing Layer (C) and a Layer (D) Containing a Water-soluble Resin (E)

1. Lamination of a Layer (D) Containing a Water-soluble Resin (E) and a Polylactic Acid Resin-containing Layer (C)

On one surface of a base material, a layer (D) containing a water-soluble resin (E) and a polylactic acid resin-containing layer (C) are laminated in this order.

Although the lamination method is not particularly restricted, a gravure coating, a direct lip coating, a slot coating, a comma coating, an ink jet, a silk screen printing or the like can be exemplified. Although the base material is not particularly restricted, a glass plate, a metal plate, a plastic film or the like can be exemplified, and from the viewpoint of economy, it is desired to use a plastic film as the base material film, and in particular, a plastic film having a surface smoothness is desired.

When a biaxially oriented film of a polyester such as polyethylene terephthalate or a polyolefin such as polypropylene is used as the base material, any method of off-line coating for coating after the film formation process of the biaxially oriented film and in-line coating for coating in the film formation process of the biaxially oriented film may be used.

When in-line coating is used, it is preferred to perform the coating before the film is thermoset. The thermosetting means that a film is crystallized by heat treating the oriented film at a condition keeping the film at a temperature higher than the stretching temperature and lower than the melting point of the film. Therefore, a coating applied to a non-oriented film, a film after uniaxial stretching in the longitudinal direction or the transverse direction, or a film after biaxial stretching is preferred. A coating applied to a film immediately after uniaxial stretching is more preferred, and it is further preferred to further stretch the film in one or more axial directions and thermoset it. As the method for drying a coating layer, a heated roll contacting method, a heat medium (air, oil and the like) contacting method, an infrared heating method, a microwave heating method and the like can be utilized.

As the method of forming a coating layer on the base material film by off-line coating, from the point of being able to coat a thin layer at a high speed, a method of gravure coating, reverse coating, spray coating, kiss coating, comma coating, die coating, knife coating, air knife coating or metering bar coating a solution prepared by dispersing a component of a coating layer in various kinds of solvents is preferred. The base material film is more preferably applied before coating with a adherence promoting treatment of, for example, a corona discharge treatment in air, in nitrogen gas, or under an atmospheric condition of nitrogen/carbon dioxide mixed gas or another gas, a plasma treatment under a pressure reduced condition, a flame treatment, a ultraviolet treatment or the like. Furthermore, an anchoring treatment may be applied using an anchoring treatment agent such as a urethane resin, an epoxy resin or a polyethylene imine.

It is preferred that the drying of the coating layer of the layer (D) containing a water-soluble resin (E) is performed at 60° C. to 180° C. in off-line coating, and at 80° C. to 250° C. in in-line coating. The time for drying is preferably 1 second to 60 seconds, more preferably 3 seconds to 30 seconds.

It is preferred that the drying of the coating layer of the polylactic acid resin is performed at 60° C. to 110° C. in off-line coating, and at 80° C. to 180° C. in in-line coating.

The time for drying is preferably 1 second to 60 seconds, more preferably 3 seconds to 30 seconds.

2. Isolation of Layer (D) Containing a Water-soluble Resin (E) from Base Material Next, by mechanical delamination at the interface between the base material and the layer (D) containing a water-soluble resin (E), the layer (D) containing a water-soluble resin (E) or the laminated layer of the layer (D) containing a water-soluble resin (E) and the polylactic acid resin-containing layer (C) is obtained.

3. Fixing of Laminated Layer to Supporting Material

Further, the obtained single layer or laminated layer is set such that the polylactic acid resin-containing layer (C) and the supporting material come into contact with each other. Although the supporting material is not particularly restricted, a glass plate, a metal plate, a plastic film and the like can be exemplified, and from the viewpoint of economy, it is preferred to use a plastic film as the supporting material, in particular, a plastic film having a surface release property.

4. Dissolution of Surface of Layer (D) Containing a Water-soluble Resin (E) or Fibrous Structure (B)

Next, an aqueous solution is applied to the layer (D) containing a water-soluble resin (E) or the fibrous structure (B) containing a water-soluble resin (A) to dissolve a part of the surface layer. Further, the layer (D) containing a water-soluble resin (E) may be completely removed by this process.

Although the aqueous solution is not particularly restricted, a purified water, an alcohol aqueous solution, a mineral dispersion, a chemical dispersion and the like can be exemplified, and from the viewpoint of economy, a purified water is desired.

5. Fixing of Fibrous Structure (B) Containing a Water-soluble Resin (A)

Although the lamination method of the single layer or the laminated layer and the fibrous structure (B) is not particularly restricted, there are a method for spraying water or an aqueous solution to the surface of the layer (D) containing a water-soluble resin (E) in the laminated layer of the layer (D) containing a water-soluble resin (E) and the polylactic acid resin-containing layer (C) or to the surface of the fibrous structure (B) to dissolve it, and bringing the dissolved surface into contact with a surface side of one of the respective layers containing a water-soluble resin to weld the respective surfaces; a method for spraying water or an aqueous solution to the surface of the single layer of the polylactic acid resin-containing layer (C) after forming the single layer of the polylactic acid resin-containing layer (C), thereafter, bringing it into contact with the fibrous structure (B), and dissolving the surface of the fibrous structure (B) contacted to the polylactic acid resin-containing layer (C) to bond them and the like.

Method of Spraying Water or Aqueous Solution

Although the above-described spraying method of water or aqueous solution is not particularly restricted, it may be able to uniformly and broadly disperse a liquid at a fine form using a sprayer such as a spray or a shower and, for example, an accumulator spray method, a nozzle spray method (two-fluid nozzle, three fluid nozzle or four-fluid nozzle), an ink jet method and the like can be used.

Lamination Method

As the lamination method, the following two kinds of methods are preferred:

Lamination method A: lamination method wherein the fibrous structure (B) and the single layer of the polylactic acid resin-containing layer (C) or the laminated layer of the layer (D) containing a water-soluble resin (E) and the polylactic acid resin-containing layer (C) are laminated at a condition being fixed onto separated respective flat plates.

Lamination method B: lamination method wherein the fibrous structure (B) and the single layer of the polylactic acid resin-containing layer (C) or the laminated layer of the layer (D) containing a water-soluble resin (E) and the polylactic acid resin-containing layer (C) are stuck to each other and laminated by being nipped between two rollers.

Coating Material Containing Water-soluble Resin (A) or Water-soluble Resin (E)

A coating material containing a water-soluble resin (A) or a water-soluble resin (E) can be used when the laminated layer of the layer (D) containing a water-soluble resin (E) and the polylactic acid resin-containing layer (C) is laminated with the fibrous structure (B) containing a water-soluble resin (A).

As the coating material containing a water-soluble resin (A) or a water-soluble resin (E), a solution uniformly dissolved with components is preferred. As a solvent, water or a mixed solution of water and a lower alcohol is preferably used. It is more preferred to use a mixed solution of water and a lower alcohol.

The concentration of solid components of the coating material containing a water-soluble resin (A) or a water-soluble resin (E) is preferably 1.0 mass % or more and 15 mass % or less, from the viewpoint of productivity such as viscosity, drying efficiency and coatability of the coating material. If a high-concentration coating material more than 15 mass % is used, the viscosity of the solution becomes too high, and there is a possibility that it becomes difficult to control the thickness of the layer (D) containing a water-soluble resin (E). When a low-concentration coating material less than 1.0 mass %, a method of adding a low-boiling point solvent having a high volatility and a compatibility with water to the solvent of the coating material, a method of performing the drying of the coating layer at a temperature of water boiling point or higher, or the like, is employed.

Further, to provide an application ability, another water-soluble organic compound as a third component may be contained in the mixed solvent as long as its content is within a range at which the stability of the coating material containing a water-soluble resin (A) or a water-soluble resin (E) can be maintained. As the water-soluble organic compound, for example, alcohols such as methanol, ethanol, n-propanol and isopropanol, glycols such as ethylene glycol and propylene glycol, glycol derivatives such as methyl cellosolve, ethyl cellosolve and n-butyl cellosolve, polyhydric alcohols such as glycerin and wax groups, ethers such as dioxane, esters such as ethyl acetate, ketones such as methyl ethyl ketone and the like can be raised. Further, the pH of the dispersion is preferably 2 to 11 from the point of stability of the solution.

Coating Material Containing Polylactic Acid Resin

As the coating material containing a polylactic acid resin, a solution uniformly dissolved with components is preferred. Although its solvent is not particularly restricted, it is preferred to use at least a sole solvent or a solution mixed with two or more kinds selected from the group consisting of butyl alcohol, chloroform, cyclohexane, acetonitrile, dichloromethane, dichloroethane, ethyl acetate, ethyl ether, dipropyl ether and toluene. From the viewpoint of productivity and handling ability, ethyl acetate is particularly preferred.

Although the solid-component concentration of the coating material containing a polylactic acid resin is not particularly restricted, it is preferably 1.0 mass % or more and 10 mass % or less, from the viewpoint of the productivity such as viscosity, drying efficiency and coatability of the coating material.

Further, to provide an application ability, another organic compound as a third component may be contained in the solution as long as its content is within a range at which the stability of the coating material containing a polylactic acid resin can be maintained.

Method of Preparing Coating Material

Although the methods of preparing the coating material containing a water-soluble resin (A) or a water-soluble resin (E) and for preparing the coating material containing a polylactic acid resin are not particularly restricted, when various kinds of additives such as crosslinking agent and particles are added within a range at which the desired effects are not damaged, it is preferred that the resin and the additives are dispersed uniformly in the coating material. As needed, may be employed a method of enhancing the solubility of the resin by raising the temperature of the solvent using a heater or the like, or a method of employing a mechanically forcible dispersion treatment using a device such as homo mixer, a jet agitator, a ball mill, a bead mill, a kneader, a sand mill or a three-roll mechanism.

Method of Using Laminate

In an operation for an abdominal cavity, it is more preferable than laparotomy to open a small hole on the abdominal cavity and perform the operation using an endoscope, because the invasiveness to the human body is smaller. In this case, a laminate is to be stuck to a target part through a thin cylindrical vessel such as a trocar. In such a case, since the laminate is good in passing property through the trocar and extensibility of the laminate after passing through the trocar, the laminate can particularly suitably used to an operation using an endoscope. ("Good in extensibility" means that the laminate once pressed into a trocar can be easily extended to an original form by a forceps or the like after being passed through the trocar.)

The laminate has a structure, for example, as shown in FIG. 1. Namely, it is a laminate 3 having at least one polylactic acid resin-containing layer (C) 2 with a predetermined thickness on at least one surface of a fibrous structure (B) 1 containing a water-soluble resin (A).

Figure 2:
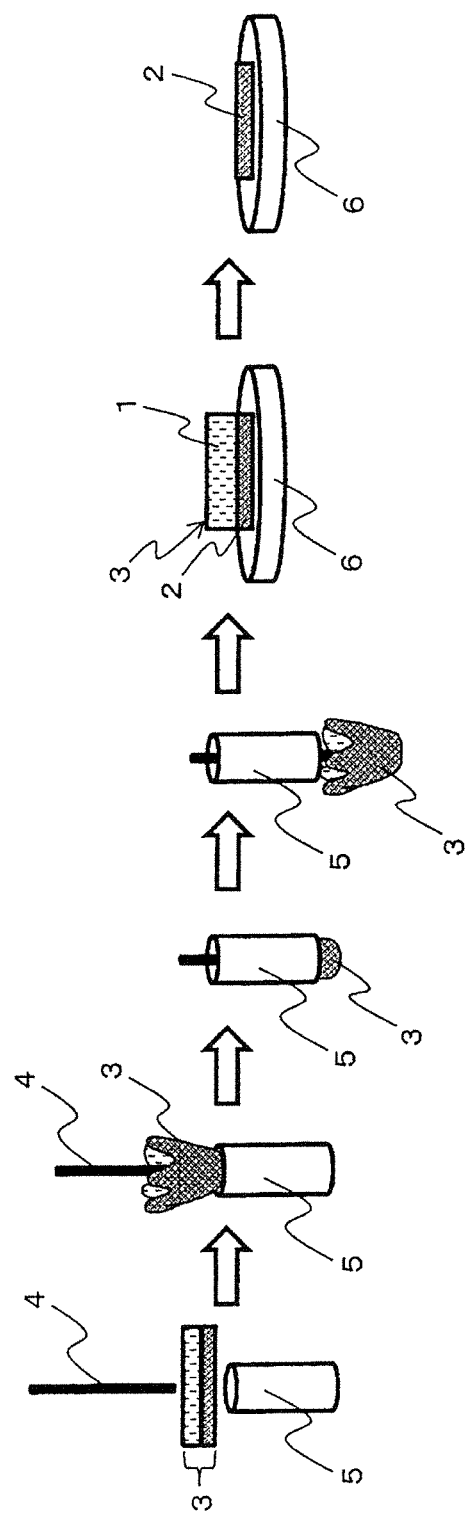
FIG. 2 is a schematic diagram showing an example of a method of using a laminate.

As the method of using the laminate, a using method shown in FIG. 2 is exemplified as an example. Namely, it is a method of using the laminate for pressing the laminate 3 into a cylindrical vessel 5 using a pressing jig 4 from one opening of the vessel 5, sending the laminate 3 out of the other opening, after sticking the laminate 3 to a surface of an adherend 6, applying a liquid onto the laminate 3 to dissolve the fibrous structure (B) 1 (shown in FIG. 1), thereby removing the fibrous structure (B), and leaving the polylactic acid resin-containing layer (C) 2 (shown in FIG. 1) on the surface of the adherend 6.

Uses

The laminate can be suitably used for medical applications such as wound-dressing membranes or adhesion-preventing membranes capable of being used in an organism or even under an environment adhered with moisture.

EXAMPLES

Hereinafter, Examples and Comparative Examples (Examples 1-12 and Comparative Examples 1-8) with respect to our laminate and Examples and Comparative Examples (Examples 13-16 and Comparative Examples 9-13) with respect to the method of producing our laminate will be explained. First, the methods of evaluating the properties are as follows:

(1) Areal Weight of Fibrous Structure (B)

The areal weight was determined based on the method described in JIS L 1096 8.3.2 (1999).

(2) Thickness of Laminate, Fibrous Structure (B), Layer (D) Containing Water-soluble Resin (E) and Polylactic Acid Resin-Containing Layer (C)

In being determined from a state of a laminate, first, a dial thickness gauge (supplied by OZAKI MFG. CO., LTD., product name: "Peacock H," amount of scale: 0.01 mm, measurement force: 1.8N or less) was used, and an average value of 10 measurement points of each sample was determined to be a total thickness of the laminate. However, when the total thickness is less than 0.05 mm, a dial thickness gauge higher in accuracy (supplied by Teclock Corporation, type: SM-1201L, amount of scale: 0.001 mm, measurement force: 1.5N or less) was used.

Next, to determine the thickness of each layer, a perpendicular section in the thickness direction was prepared by a microtome, and the section was observed using a scanning electron microscope (SEM, supplied by Keyence Corporation, VE-7800) and appropriately adjusting the magnification to 2,500 times to 100,000 times so that each observed layer was put within 10% to 90% of the angle of visibility. The thickness of each layer was determined as an average of values measured at different 10 sections of an identical sample. When a thickness of each layer became 0.1 µm or less and it was difficult to observe by the above-described method, it was similarly observed using a high-resolution transmission electron microscope (supplied by JEOL Ltd., JEM-2100) and adjusting the magnification in a range of 500,000 times to 1,000,000 times. When the determination was still difficult even by the method, the thickness was determined by storing the observed image and appropriately enlarging the image (for example, by printing it at an A3 size or the like). The thickness of a fibrous structure (B) was determined as a thickness calculated by subtracting the thicknesses of a layer (D) containing water-soluble resin (E) and a polylactic acid resin-containing layer (C) from the total thickness of the laminate. The thickness of a fibrous structure (B) in case having a reinforcing layer was determined as a thickness calculated by subtracting the thicknesses of a layer (D) containing water-soluble resin (E), a polylactic acid resin-containing layer (C) and the reinforcing layer from the total thickness of the laminate. Namely, the thickness of a fibrous structure (B) when having a reinforcing layer means a thickness of only the fibrous structure (B) that does not include the thickness of the reinforcing layer.

(3) Evaluation of Dissolvability of Fibrous Structure (B)

The height from a surface of a test piece to a tip of a burette was adjusted to 10 mm. The timing when one drop of water was dropped from the burette to one surface of the test piece of a fibrous structure (B) was referred to as a starting time, the timing when the water permeated to another surface thereof and dissolved it was referred to as a finishing time, and a time required from the starting time until the finishing time was determined. Dissolution means that the shape of the fibers cannot be maintained and collapses, and it is determined by observing from various directions. When the time required until the finishing of dissolution was 10 seconds or more and less than 5 minutes was determined to be Rank A, 5 minutes or more was determined to be Rank B, and less than 10 seconds was determined to be Rank C.

(4) Workability:
(a) Stickiness
Two sheets of Si rubbers (supplied by Kyowa Industrial Co., Ltd., hardness: 20 degrees, 3 cm×1 cm) were prepared, and purified water was sprayed onto the surfaces of the two sheets of Si rubbers to uniformly adhere thereto at an amount of 5 mg per each sheet under an environment of a temperature of 23±5° C. and a relative humidity of 65±20%.

Thereafter, a test piece of 5 cm×5 cm was nipped by two sheets of wet Si rubbers for 1 second at a force of 5N, and was held in the air so that the longer sides of the Si rubbers were perpendicular to the ground, and when one Si rubber was fixed and the other Si rubber was exfoliated in the horizontal direction relative to the ground at a speed of 1.5 m/min., it was checked whether the test piece fell without being stuck to the Si rubber or not. When it separated from the Si rubber and fell was determined to be Rank A, when it stuck to the Si rubber and did not fall and a breakage did not occur in the test piece was determined to be Rank B, and when it stuck to the Si rubber and did not fall and a breakage occurred in the test piece was determined to be Rank C.

(b) Trocar Passing Property:
A test piece of 9 cm×12 cm and a trocar used in a general laparoscopic surgery were used, and flexibility was evaluated at the following condition. Further, as the trocar and a sending-out rod, the following (i) and (ii) were used. In the sending out, the test piece was placed so that the polylactic acid resin-containing layer (C) side thereof was brought into contact with the hole part of the trocar, it was pressed into the trocar, it was evaluated whether the test piece could pass through the trocar, and further, after passing, whether the test piece could be extended to an original formation when extending it by hand. Further, supposing use during operation, a test wetting the inside of the trocar was also carried out. With respect to a test piece which did not pass through the trocar, the extensibility could not be evaluated.
  (i) Trocar: supplied by Covidien Inc., "VERSAPORT" (registered trade mark) V2, 5 mm short (hole: φ5 mm, cylinder length: 9 cm)
    Sending-out rod: acryl rod of φ2 mm having a tip adhered with a semispherical (φ2 mm) Si rubber (supplied by Kyowa Industrial Co., Ltd., hardness: 20 degrees, 3 cm×1 cm)
  (ii) Trocar: supplied by Covidien Inc., "VERSASEAL*PLUS," 12 mm (hole: 12 mm, cylinder length: 13 cm)
    Sending-out rod: acryl rod of φ3 mm having a tip adhered with a semispherical (φ3 mm) Si rubber (supplied by Kyowa Industrial Co., Ltd., hardness: 20 degrees, 3 cm×1 cm)
The evaluation was performed as shown in Table 1.
Evaluation A: Condition 1 was satisfied (tests of condition 2 and any condition thereafter were not carried out).

Evaluation B: Condition 1 was not satisfied but Condition 2 was satisfied (tests of condition 3 and any condition thereafter were not carried out).

Evaluation C: Conditions 1 and 2 were not satisfied but Condition 3 was satisfied (tests of condition 4 and any condition thereafter were not carried out).

Evaluation D: Conditions 1 to 3 were not satisfied but Condition 4 was satisfied (test of condition 5 was not carried out).

Evaluation E: Conditions 1 to 4 were not satisfied but Condition 5 was satisfied.

TABLE 1

| Condition | Used equipment | Passing property | | Extensibility | | Evaluation |
| | | In trocar Wet | In trocar Dry | In trocar Wet | In trocar Dry | |
|---|---|---|---|---|---|---|
| Condition 1 | i | Pass | Pass | Extend | Extend | A |
| Condition 2 | | Not pass | Pass | —* | Extend | B |
| Condition 3 | ii | Pass | Pass | Extend | Extend | C |
| Condition 4 | | Not pass | Pass | —* | Extend | D |
| Condition 5 | | Not pass | Not pass | —* | —* | E |

*Because of not passing through the trocar, extensibility could not be evaluated.

(c) Re-sticking Property
The polylactic acid resin-containing layer (C) side of a test piece (size: 10 cm×10 cm) was stuck to a PET (polyethylene terephthalate) film (supplied by Toray Industries, Inc., "Lumirror" (registered trade mark) #100T60, size; 5 cm×5 cm) wetted by being sprayed with 100 g of purified water, and that state was maintained for 5 seconds.

Thereafter, when the test piece was exfoliated holding a part which was not stuck, when the test piece could be easily exfoliated without causing breakage of the test piece was determined to be Rank A, when exfoliation was possible but during it an exfoliation within the test piece or shrinkage at an area of 30% or more was caused was determined to be Rank B, and when exfoliation was impossible because there was a breakage such as being torn off was determined to be Rank C.

(5) Adherence-1 (Examples 1 to 12, Comparative Examples 1 to 8)

The polylactic acid resin-containing layer (C) side of a test piece (size: 3 cm×3 cm) was stuck to a central portion of a PET film (supplied by Toray Industries, Inc., "Lumirror" (registered trade mark) #100T60, size; 5 cm×5 cm) wetted by being sprayed with 100 g of purified water, and it was adhered by pressing it with a dried Si rubber (supplied by Kyowa Industrial Co., Ltd., hardness: 20 degrees, 3 cm×1 cm) for 10 seconds. Thereafter, the test piece together with the PET film was transferred into a vessel having a bottom surface of 12 cm×5 cm, and 12 g of purified water was charged thereinto softly from a part above the test piece to dissolve and remove the fibrous structure (B). Next, the test piece together with the PET film was taken out from the solution, and it was left for one hour or more in a constant temperature and humidity vessel (supplied by Espec Corporation, LHU-113) controlled to an environment of a temperature of 25° C. and a relative humidity of 90% at a condition of being placed vertically, thereby removing excessive moisture from the test piece.

Then, the test piece together with the PET film was taken out from the constant temperature and humidity vessel, it was checked whether the test piece and the PET film could be shifted in position from each other by hand, when they were not shifted was determined to be Rank A, when they were shifted was determined to be Rank B, and a case where it could not be checked whether the test piece was shifted or elongated because of being swelled was determined to be Rank C.

(6) Appearance

A laminate was evaluated by observation. The evaluation indexes are as follows:

Evaluation A: Flatness was good, and sag, wrinkle and dissolved portion were not observed.

Evaluation B: Flatness was poor, and slight sag, wrinkle and dissolved portion were observed.

Evaluation C: Flatness was poor, and on most part, sag, wrinkle and dissolved portion or hole were observed.

(7) Adherence-2 (Examples 13 to 16, Comparative Examples 9 to 13)

Using both hands, a single layer of a polylactic acid resin-containing layer (C) or a laminated layer of a layer (D) containing a water-soluble resin (E) and a polylactic acid resin-containing layer (C), and a fibrous structure (B), were separated from each other, and it was served to a sensory evaluation. The evaluation indexes are as follows:

Evaluation A: Separation between the single layer or the laminated layer and the fibrous structure (B) is difficult, and material breakage occurs on the whole of at least one of the single layer or the laminated layer and the fibrous structure (B).

Evaluation B: Separation between the single layer or the laminated layer and the fibrous structure (B) is difficult a little, and slight material breakage occurs partially on at least one of the single layer or the laminated layer and the fibrous structure (B).

Evaluation C: Separation between the single layer or the laminated layer and the fibrous structure (B) can be easily performed, and slight material breakage occurs partially on at least one of the single layer or the laminated layer and the fibrous structure (B), or material breakage does not occur.

(8) Environmental Load (Used Amount of Organic Solvent) (Examples 13 to 16, Comparative Examples 9 to 13)

The evaluation indexes are as follows:

Evaluation A: Used amount of organic solvent at the time of lamination working is less than 5 g/m².

Evaluation B: Used amount of organic solvent at the time of lamination working is 5 g/m² or more and less than 100 g/m².

Evaluation C: Used amount of organic solvent at the time of lamination working is 100 g/m² or more.

(9) Workability of Lamination (Heating Temperature) (Examples 13 to 16, Comparative Examples 9 to 13)

The evaluation indexes are as follows:

A: At the time of lamination working, a heating material with a temperature of 50° C. or higher is not used.

B: At the time of lamination working, a heating material with a temperature of 50° C. or higher and lower than 100° C. is used.

C: At the time of lamination working, a heating material with a temperature of 100° C. or higher is used.

Hereinafter, the materials used in Examples 1 to 12 and Comparative Examples 1 to 8 and the materials used in Examples 13 to 16 and Comparative Examples 9 to 13 and the apparatus used therefor will be explained respectively.

First, the materials used in Examples 1 to 12 and Comparative Examples 1 to 8 will be explained.

Used Base Material Film (PET-1):

Biaxially oriented polyester film (supplied by Toray Industries, Inc., "Lumirror" (registered trade mark) type: T60, thickness: 100 µm).

Used Polylactic Acid Resin (PLA-1):

Poly-L-lactic acid-D-lactic acid copolymerized resin with an amount of poly-D-lactic acid at 50 mol %, having no melting point (amorphous), and having a weight average molecular weight calculated by conversion with PMMA of 400,000 (supplied by PURAC Corporation, PURASORB PDL20).

(PLA-2):

Poly-L-lactic acid resin with an amount of poly-D-lactic acid at 1.4 mol %, having a melting point of 150° C., and having a weight average molecular weight calculated by conversion with PMMA of 220,000 (supplied by Nature Works Corporation, 4032D).

Used Water-soluble Resin (A), Water-soluble Resin (E)

(Pullulan-1):

Pullulan having a number average molecular weight of about 200,000 daltons and a viscosity in a range of 100 to 180 mm²/sec. (aqueous solution with a temperature of 30° C. and a solid component concentration of 10 mass %) (sold by Hayashibara Co., Ltd., Pullulan Pl-20).

(PVA-1):

Polyvinyl alcohol having a degree of saponification of 96.5 mol % and a viscosity of 27.5 mPa·s (4 mass % aqueous solution, 20° C.) (supplied by Japan Vam & Poval Co., Ltd., JM-17).

(Gelatin-1):

Gelatin powder (supplied by Nitta Gelatin Inc., for medical applications).

(Collagen-1):

Pig-derived collagen powder (supplied by Nippon Meat Packers, Inc., SOFD type).

Used Fibrous Structure (B)

(Structure-1):

Using Pullulan-1 as a water-soluble resin (A), a nonwoven fabric having an areal weight of 50 g/m² and a thickness of 300 µm was prepared by melt-blow system.

(Structure-2):

Using Pullulan-1 as a water-soluble resin (A), a nonwoven fabric having an areal weight of 1 g/m² and a thickness of 10 µm was prepared by melt-blow system.

(Structure-3):

Using PVA-1 as a water-soluble resin (A), a nonwoven fabric having an areal weight of 30 g/m² and a thickness of 300 µm was prepared by melt-blow system.

(Structure-4):

Using Pullulan-1 as a water-soluble resin (A), a nonwoven fabric having an areal weight of 200 g/m² and a thickness of 1,000 µm was prepared by melt-blow system.

(Structure-5):

Using Pullulan-1 as a water-soluble resin (A), a nonwoven fabric having an areal weight of 1,000 g/m² and a thickness of 5,000 µm was prepared by melt-blow system.

(Structure-6):

Using Pullulan-1 as a water-soluble resin (A), a nonwoven fabric having an areal weight of 1,500 g/m² and a thickness of 6,000 µm was prepared by melt-blow system.

(Structure-7):

Using Collagen-1 as a water-soluble resin (A), a nonwoven fabric having an areal weight of 10 g/m² and a thickness of 80 µm was prepared by wet-spinning system.

(Structure-8):

Using Pullulan-1 as a water-soluble resin (A), a nonwoven fabric having an areal weight of 300 g/m² and a thickness of 1,700 μm was prepared by melt-blow system.

Figure 3:
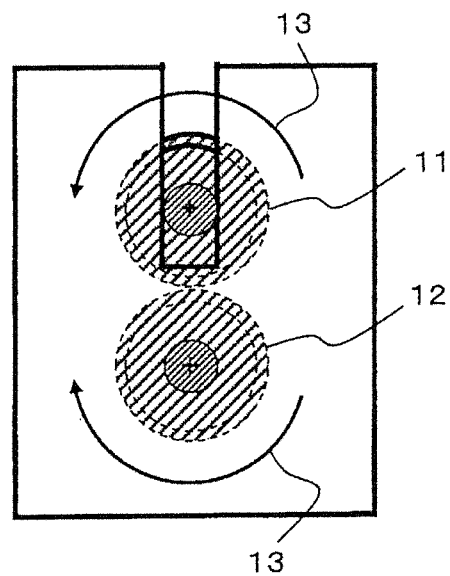
FIG. 3 is a schematic diagram showing rollers used for a method of producing a laminate.

Next, the materials and the apparatus used in Examples 13 to 16 and Comparative Examples 9 to 13 will be explained.
Used Base Material Film
(PET-1) (Same Base Material Film as Aforementioned):
Biaxially oriented polyester film (supplied by Toray Industries, Inc., "Lumirror" (registered trade mark) type: T60, thickness: 100 μm).
Resin Used for Polylactic Acid Resin-containing Layer (C)
(PLA-3):
Poly-L-lactic acid resin with an amount of poly-D-lactic acid at 12 mol %, having a melting point of 150° C., and having a weight average molecular weight calculated by conversion with PMMA of 220,000 (supplied by Nature Works Corporation, 4060D).
Used Water-soluble Resin (A)
(PVA-2):
Polyvinyl alcohol having a degree of saponification of 88 mol % and a viscosity of 5 mPa·s (4 mass % aqueous solution, 20° C.) (supplied by Nippon Synthetic Chemical Industry Co., Ltd., "GOHSENOL" (registered trade mark) EG-05P).
Used Fibrous Structure (B)
Using PVA-2, a nonwoven fabric having an areal weight of 30 g/m² and a thickness of 300 μm was prepared by melt-blow system. It was sampled at a size of 100 mm×100 mm. Aqueous solution containing water-soluble resin as provided aqueous solution
Using a warming homogenizer, PVA-2 was dissolved into water to prepare a water-soluble resin emulsion solution with a solid component concentration of 1 mass %.
Flat Plate Used for Lamination Method A
(Flat Plate-1):
Used was a SUS304 plate having a thickness of 5 mm, a size of 300 mm×300 mm and a surface finish of 2B.
Roller Used for Lamination Method B
As shown in FIG. 3, two rubber rollers (11, 12), each formed using an aluminum as its roller core material and a nitrile rubber (NBR, hardness: 30 degrees) as its surface material and each having a diameter of 5 cm, a width of 30 cm and a weight of 1 kg, were set at their axes, rotatably in the directions capable of being contacted with each other (rotational directions 13). The upper roller 11 was set such that its shaft can move in the vertical direction so that only its self-weight applies to the lower roller 12.
Sprayer Used for Lamination
An accumulator-type sprayer (supplied by Maruhachi Industrials) was used.

Example 1

Using a warming homogenizer, Pullulan-1 as a water-soluble resin was dissolved in water to prepare an water-soluble resin emulsion solution, it was applied to one surface of a base material film PET-1 by applicator method so that the layer thickness after drying became 3 μm, and it was dried in a hot air-drying type drier at 90° C. for 20 seconds to form a layer (D) containing a water-soluble resin (E) on the base material film.

Further, as a polylactic acid resin-containing layer (C), a solution dissolved with PLA-1 to ethyl acetate was applied onto the layer (D) containing a water-soluble resin (E) using a metering bar so that the layer thickness after drying became 150 nm, it was dried in a hot air-drying type drier at 80° C. for 20 seconds to provide the polylactic acid resin-containing layer (C) thereon, and thus a laminated layer was formed.

The laminated layer comprising the water-soluble resin (E) and the polylactic acid resin was exfoliated from the base material film, and after purified water was applied to the layer (D) containing the water-soluble resin (E) by a sprayer to achieve 5 g/m², it was quickly laminated to Structure-1. The evaluation results of the obtained structure and the laminate laminated with the laminated layer are shown in Table 2.

Example 2

A laminate laminated with the fibrous structure (B) and the polylactic acid resin-containing layer (C) was formed similarly to Example 1 other than a condition where the thickness of the polylactic acid resin-containing layer (C) was controlled at 50 nm.

Example 3

A laminate laminated with the fibrous structure (B) and the polylactic acid resin-containing layer (C) was formed similarly to Example 1 other than a condition where the thickness of the polylactic acid resin-containing layer (C) was controlled at 10 nm and the layer thickness after drying of the layer (D) containing the water-soluble resin (E) was controlled at 1 μm.

Example 4

A laminate laminated with the fibrous structure (B) and the polylactic acid resin-containing layer (C) was formed similarly to Example 1 other than a condition where the thickness of the polylactic acid resin-containing layer (C) was controlled at 500 nm and the layer thickness after drying of the layer (D) containing the water-soluble resin (E) was controlled at 1 μm.

Example 5

A laminate laminated with the fibrous structure (B) and the polylactic acid resin-containing layer (C) was formed similarly to Example 1 other than a condition where the layer (D) containing the water-soluble resin (E) was applied so that its layer thickness became 0.01 μm.

Example 6

A laminate laminated with the fibrous structure (B) and the polylactic acid resin-containing layer (C) was formed similarly to Example 1 other than a condition where the layer (D) containing the water-soluble resin (E) was applied so that its layer thickness became 15 μm.

Example 7

A laminate laminated with the fibrous structure (B) and the polylactic acid resin-containing layer (C) was formed similarly to Example 1 other than a condition where not Structure-1 but Structure-2 was employed as the fibrous structure (B).

Example 8

A laminate laminated with the fibrous structure (B) and the polylactic acid resin-containing layer (C) was formed similarly to Example 1 other than a condition where not Structure-1 but Structure-3 was employed as the fibrous structure (B), PVA-1 was used for the layer (D) containing the water-soluble resin (E) and the layer thickness after drying of the layer (D) was controlled at 3 μm.

Example 9

A laminate laminated with the fibrous structure (B) and the polylactic acid resin-containing layer (C) was formed similarly to Example 1 other than a condition where not Structure-1 but Structure-4 was employed as the fibrous structure (B).

Example 10

A laminate laminated with the fibrous structure (B) and the polylactic acid resin-containing layer (C) was formed similarly to Example 1 other than a condition where not Structure-1 but Structure-5 was employed as the fibrous structure (B).

Example 11

A laminate laminated with the fibrous structure (B) and the polylactic acid resin-containing layer (C) was formed similarly to Example 1 other than a condition where not Structure-1 but Structure-8 was employed as the fibrous structure (B).

Example 12

A polylactic acid resin-containing layer (C) was formed at a thickness of 500 nm and a layer (D) containing a water-soluble resin (E) was formed so that its thickness after drying became 1 μm, respectively, and the obtained laminated layer was washed by water, thereby removing a layer containing the water-soluble resin. Further, a laminate laminated with the fibrous structure (B) and the polylactic acid resin-containing layer (C) was formed similarly to Example 1 other than a condition where positions applied with purified water were set at 4 corners of Structure-1.

Comparative Example 1

A laminate laminated with the fibrous structure (B) and the polylactic acid resin-containing layer (C) was formed similarly to Example 1 other than a condition where the thickness of the polylactic acid resin-containing layer (C) was controlled at 1,000 nm.

Comparative Example 2

Similarly to Example 1, a layer (D) containing a water-soluble resin (E) was formed and a laminated layer was formed. Thereafter, although, to use PLA-2 for a polylactic acid resin-containing layer (C), it was tried to dissolve PLA-2 into heated ethyl acetate (60° C. to 90° C.), coating could not be carried out because PLA-2 did not dissolve into the ethyl acetate.

Comparative Example 3

Similarly to Example 1 other than a condition where a Gelatin-1 layer was formed instead of a polylactic acid resin-containing layer (C) and its thickness was controlled at 1,000 nm, a laminate laminated with the fibrous structure (B) and the gelatin layer was formed.

Comparative Example 4

A laminate laminated with the fibrous structure (B) and the polylactic acid resin-containing layer (C) was formed similarly to Example 1 other than a condition where the thickness of the polylactic acid resin-containing layer (C) was controlled at 1,000 nm and the thickness of the layer (D) containing the water-soluble resin (E) was controlled at 30 μm.

Comparative Example 5

A laminate laminated with the fibrous structure (B) and the polylactic acid resin-containing layer (C) was formed similarly to Example 1 other than a condition where the thickness of the polylactic acid resin-containing layer (C) was controlled at 1,000 nm and not Structure-1 but Structure-6 was employed as the fibrous structure (B).

Comparative Example 6

A laminate laminated with the fibrous structure (B) and the polylactic acid resin-containing layer (C) was formed similarly to Example 1 other than a condition where the thickness of the polylactic acid resin-containing layer (C) was controlled at 1,000 nm, Collagen-1 was employed for a layer (D) containing a water-soluble resin (E), and not Structure-1 but Structure-7 was employed as the fibrous structure (B).

Comparative Example 7

Similarly to Example 1 other than a condition where a pullulan layer was formed instead of a polylactic acid resin-containing layer (C) and its thickness was controlled at 300 nm, a laminate laminated with the fibrous structure (B) and the pullulan layer was formed.

Comparative Example 8

Similarly to Example 1 other than a condition where the working was finished when the laminated layer comprising the water-soluble resin (E) and the polylactic acid resin was exfoliated from the base material film and the lamination working with the fibrous structure (B) was not carried out, a laminated layer of the polylactic acid resin-containing layer (C) was formed.

The results of characteristics of Examples 1 to 12 and Comparative Examples 1 to 8 are described in Tables 2 to 5.

TABLE 2

|  |  |  | Example 1 | Example 2 | Example 3 | Example 4 | Example 5 | Example 6 |
|---|---|---|---|---|---|---|---|---|
| Polylactic acid resin- containing layer (C) | Resin | Unit | PLA-1 | PLA-1 | PLA-1 | PLA-1 | PLA-1 | PLA-1 |
|  | Thickness | nm | 150 | 50 | 10 | 500 | 150 | 150 |
| Layer (D) containing water-soluble resin (E) | Resin | — | Pullulan-1 | Pullulan-1 | Pullulan-1 | Pullulan-1 | Pullulan-1 | Pullulan-1 |
|  | Thickness | μm | 3 | 3 | 1 | 1 | 0.01 | 15 |

TABLE 2-continued

|  |  |  |  |  |  |  |  |  |
|---|---|---|---|---|---|---|---|---|
| Fibrous structure (B) containing water-soluble resin (A) | Resin | — | Pullulan-1 | Pullulan-1 | Pullulan-1 | Pullulan-1 | Pullulan-1 | Pullulan-1 |
|  | Areal weight | g/m² | 50 | 50 | 50 | 50 | 50 | 50 |
|  | Thickness | μm | 300 | 300 | 300 | 300 | 300 | 300 |

|  |  |  | Example 7 | Example 8 | Example 9 | Example 10 | Example 11 | Example 12 |
|---|---|---|---|---|---|---|---|---|
| Polylactic acid resin-containing layer (C) | Resin | Unit | PLA-1 | PLA-1 | PLA-1 | PLA-1 | PLA-1 | PLA-1 |
|  | Thickness | nm | 150 | 150 | 150 | 150 | 150 | 500 |
| Layer (D) containing water-soluble resin (E) | Resin | — | Pullulan-1 | PVA-1 | Pullulan-1 | Pullulan-1 | Pullulan-1 | None |
|  | Thickness | μm | 3 | 3 | 3 | 3 | 3 | (Non-layer state) |
| Fibrous structure (B) containing water-soluble resin (A) | Resin | — | Pullulan-1 | PVA-1 | Pullulan-1 | Pullulan-1 | Pullulan-1 | Pullulan-1 |
|  | Areal weight | g/m² | 1 | 30 | 200 | 1,000 | 300 | 50 |
|  | Thickness | μm | 10 | 300 | 1,000 | 5,000 | 1,700 | 300 |

TABLE 3

|  |  |  | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|
| Polylactic acid resin-containing layer (C) | Resin | Unit | PLA-1 | PLA-2 | Gelatin-1 | PLA-1 | PLA-1 | PLA-1 | Pullulan-1 | PLA-1 |
|  | Thickness | nm | 1,000 | — | 1,000 | 1,000 | 1,000 | 1,000 | 300 | 150 |
| Layer (D) containing water-soluble resin (E) | Resin | — | Pullulan-1 | — | Pullulan-1 | Pullulan-1 | Pullulan-1 | collagen-1 | Pullulan-1 | Pullulan-1 |
|  | Thickness | μm | 3 | — | 3 | 30 | 3 | 3 | 3 | 3 |
| Fibrous structure (B) containing water-soluble resin (A) | Resin | — | Pullulan-1 | — | Pullulan-1 | Pullulan-1 | Pullulan-1 | collagen-1 | Pullulan-1 | None |
|  | Areal weight | g/m² | 50 | — | 50 | 50 | 1,500 | 10 | 50 | — |
|  | Thickness | μm | 300 | — | 300 | 300 | 6,000 | 80 | 300 | — |

TABLE 4

|  | Example 1 | Example 2 | Example 3 | Example 4 | Example 5 | Example 6 |
|---|---|---|---|---|---|---|
| (Fibrous structure) Dissolvability | A | A | A | A | A | A |
| Stickiness | A | A | A | A | A | A |
| Trocar passing property | A | A | A | A | A | A |
| Re-sticking property | A | A | A | A | B | A |
| Adherence-1 | A | A | A | A | A | A |

|  | Example 7 | Example 8 | Example 9 | Example 10 | Example 11 | Example 12 |
|---|---|---|---|---|---|---|
| (Fibrous structure) Dissolvability | A | A | A | A | A | A |
| Stickiness | A | A | A | A | A | A |
| Trocar passing property | A | A | C | C | C | C |
| Re-sticking property | B | A | A | A | A | B |
| Adherence-1 | A | A | A | A | A | A |

TABLE 5

|  | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| (Fibrous structure) Dissolvability | A | — | A | A | B | C | A | — |
| Stickiness | A | — | C | A | A | C | B | B |
| Trocar passing property | A | — | D | C | E | D | D | E |
| Re-sticking property | A | — | C | A | A | B | C | B |
| Adherence-1 | B | — | C | B | B | B | C | A |

In Examples 1 to 12, the evaluations of dissolvability of fibrous structure (B), stickiness, trocar passing property, re-sticking property and adherence were good. In Comparative Examples 1 to 8, there were poor points in any of the items. Points to be specially mentioned will be described.

With respect to trocar passing property, in Comparative Examples 3 and 7, because the surface provided with trocar holes was formed not from a non-water-soluble resin (polylactic acid resin), but from a water-soluble resin (gelatin, pullulan), in case where there was moisture in the trocar, the resin layer swelled, broke, and passing became impossible. Further, in Comparative Example 8, the strength of layer was poor, the layer broke, and passing was impossible.

With respect to adherence, in Comparative Examples 3 and 7, because the whole of the laminate was formed from a water-soluble resin, it swelled, and the evaluation of adherence was Rank C. Further, in Comparative Examples 4 and 5, the thicknesses were out of our range, respectively, and because the water-soluble resin could not be removed sufficiently, the evaluation of adherence was Rank B.

Example 13

Using a warming homogenizer, PVA-2 was dissolved in water to prepare an water-soluble resin emulsion solution, it was applied to one surface of a base material film PET-1 using a metering bar so that the layer thickness after drying became 3 µm, and it was dried in a hot air-drying type drier at 90° C. for 20 seconds to form a layer (D) containing a water-soluble resin on the PET-1.

Further, as a polylactic acid resin-containing layer (C), a solution dissolved with PLA-3 to ethyl acetate was applied onto the layer (D) containing a water-soluble resin using a metering bar so that the layer thickness after drying became 500 nm, and it was dried in a hot air-drying type drier at 70° C. for 20 seconds to provide the polylactic acid resin-containing layer (C) thereon.

The planar structure laminated with the PET-1, the layer (D) containing a water-soluble resin and the polylactic acid resin-containing layer (C) was sampled at a size of 100 mm×100 mm, it was dipped in purified water to dissolve the, and a single substance of the polylactic acid resin-containing layer (C) was obtained.

The following operation was carried out under a regular-temperature and regular-humidity environment (20° C.±15° C., 65% RH±20% RH).

Using two sheets of Flat plate-1, the fibrous structure (B) and the polylactic acid resin-containing layer (C) were fixed to each surface of separated flat plates, and to the fibrous structure (B), purified water was sprayed using a sprayer so that the purified water was distributed over the whole of the surface of the base material having a size of 100 mm×100 mm at 5 g/m². Thereafter, while maintaining the parallel state between the fibrous structure (B) and the polylactic acid resin-containing layer (C), they were quickly laminated so that the four positions of their four corners were approximately coincided. The evaluation result is as shown in Table 6.

Example 14

The following operation was carried out under a regular-temperature and regular-humidity environment (20° C.±15° C., 65% RH±20% RH).

Figure 4:
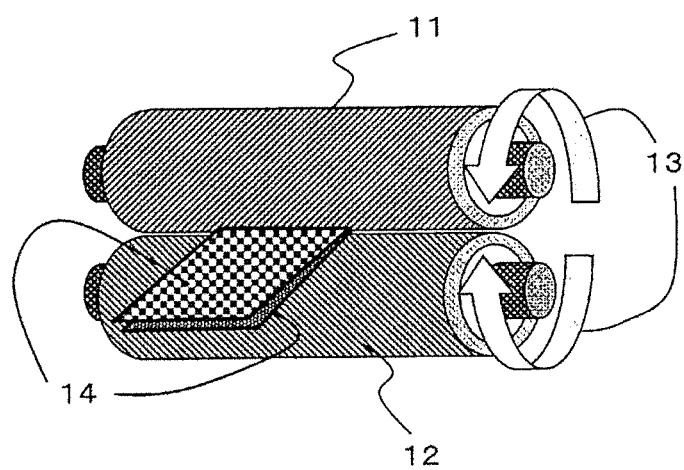
FIG. 4 is a schematic diagram showing a lamination method in Example 14.

Using two sheets of PET-1 (300 mm×300 mm), the fibrous structure (B) and a single substance of the polylactic acid resin-containing layer (C), which was prepared in a manner similar to that in Example 13, were fixed to each surface of separated PET-1. Next, to the whole of the surface of the fibrous structure (B) fixed to PET-1, purified water was sprayed using a sprayer so that the purified water was distributed over the whole of the surface of the fibrous structure (B) having a size of 100 mm×100 mm at 5 g/m². Thereafter, the fibrous structure (B) and the polylactic acid resin-containing layer (C) were quickly laminated by passing them between two rollers so that the four positions of their four corners were approximately coincided (FIG. 4). In FIG. 4, symbol 11 shows an upper roller, symbol 12 shows a lower roller, symbol 13 shows a rotational direction, and symbol 14 shows PET-1, respectively. The evaluation result is as shown in Table 6.

Example 15

The following operation was carried out under a regular-temperature and regular-humidity environment (20° C.±15° C., 65% RH±20% RH).

Using a flat structure prepared similarly to Example 13 other than a condition where the thickness after drying of the polylactic acid resin-containing layer (C) was controlled at 150 nm, a laminated layer comprising the polylactic acid resin-containing layer (C) and the layer (D) containing a water-soluble resin was physically exfoliated from PET-1. Next, the exfoliated laminated layer was sampled at a size of 100 mm×100 mm, lamination was carried out similarly to Example 13 other than a condition where the polylactic acid resin-containing layer (C) of the laminated layer was fixed to come to Flat plate-1 side. The evaluation result is as shown in Table 6.

Example 16

The following operation was carried out under a regular-temperature and regular-humidity environment (20° C.±15° C., 65% RH±20% RH).

The laminated layer prepared similarly to Example 15 was sampled at a size of 100 mm×100 mm, lamination was carried out similarly to Example 14 other than a condition where the polylactic acid resin-containing layer (C) of the laminated layer was fixed to come to Flat plate-1 side. The evaluation result is as shown in Table 6.

Reference Example 17

A single substance of the polylactic acid resin-containing layer (C) was prepared similarly to Example 13. Next, a solution controlled at a solid component concentration of 30 mass % by diluting a urethane-based adhesive (supplied by Mitsui Chemicals, Inc., main agent: "Takelac" (registered trade mark) A3216, curing agent: "Takenate" (registered trade mark) A3070) with ethyl acetate was applied onto one surface of the polylactic acid resin-containing layer (C) using a metering bar so that the layer thickness after drying became 3 µm, and it was dried in a hot air-drying type drier at 70° C. for 20 seconds to provide an adhesive layer.

Thereafter, the fibrous structure (B) and the polylactic acid resin-containing layer (C) were quickly laminated at a state where the adhesive layer was positioned between the fibrous structure (B) and the polylactic acid resin-containing layer (C), by passing them between two rollers so that the four positions of their four corners were approximately coincided. Thereafter, it was aged at 40° C. for 48 hours or more. The evaluation result is as shown in Table 7.

When the adhesive layer was dried in the hot air-drying type drier, a shrinkage occurred, and the appearance of the laminate was bad. Further, the used amount of organic solvent exceeded 5 g/m².

Reference Example 18

Using a pair of a casing drum and a polishing roller, which were rotated in the directions contacted with each other and cooled at 40° C., and a melting extruder, PLA-3 was supplied to the melting extruder, it was discharged from a T-shaped die controlled at a die temperature of 210° C. to be brought into close contact with the casting drum, thereafter, it was immediately laminated with the fibrous structure (B) placed on the surface of the polishing roller, and cooled, and then wound by a winder. As shown with the evaluation result in Table 7, in the obtained laminate, the fibers of the fibrous structure (B) were adhered to each other by heat, and the shape was deteriorated.

Reference Example 19

A single substance of the polylactic acid resin-containing layer (C) was prepared similarly to Example 13. Next, after the fibrous structure (B) and the polylactic acid resin-containing layer (C) were stacked to each other, they were passed between a pair of a heating drum and a nip roller, which were rotated in the directions contacted with each other and heated at 180° C. (corresponding to a melting point of the polylactic acid resin-containing layer (C)+about 10° C.). As shown with the evaluation result in Table 7, the obtained polylactic acid resin-containing layer (C) was fused and it could not form a layer structure.

Reference Example 20

A single substance of the polylactic acid resin-containing layer (C) was prepared similarly to Example 13. Next, a silicone-based adhesive with a thickness of 50 μm, which had been nipped by two mold release films, was exfoliated from the mold release films, it was nipped between the fibrous structure (B) and the polylactic acid resin-containing layer (C), and they were passed between two rollers similarly to Example 14 to laminate the fibrous structure (B) and the polylactic acid resin-containing layer (C). As shown with the evaluation result in Table 7, the fibrous structure (B) was easily delaminated from the adhesive.

Reference Example 21

The following operation was carried out under a regular-temperature and regular-humidity environment (20° C.±15° C., 65% RH±20% RH).

A single substance of the polylactic acid resin-containing layer (C) was prepared similarly to Reference Example 17. Next, the respective single substances of the fibrous structure (B) and the polylactic acid resin-containing layer (C) were stacked to each other, a thorny needle, which had a plurality of thorns extending downwardly toward the tip of the metal needle, was once penetrated from a fibrous structure (B) side to a polylactic acid resin-containing layer (C) side to be pressed at a condition where a part of the fibers of the fibrous structure (B) were caught by the thorns, thereafter, the needle was pulled out gently, and from the opened holy, a part of the fibrous structure (B) was exposed to the surface of the polylactic acid resin-containing layer (C). Similar operations were carried out at an interval of 5 mm so that the distances between the centers of the holes became uniform. As shown with the evaluation result in Table 7, the appearance and the adherence were poor.

TABLE 6

| | | Example 13 | Example 14 | Example 15 | Example 16 |
|---|---|---|---|---|---|
| Lamination method | | A | B | A | B |
| Fibrous structure (B) containing water-soluble resin (A) | Material | Water-soluble resin PVA-2 | Water-soluble resin PVA-2 | Water-soluble resin PVA-2 | Water-soluble resin PVA-2 |
| | Thickness (μm) | 300 | 300 | 300 | 300 |
| | Areal weight (g/m²) | 30 | 30 | 30 | 30 |
| Layer (D) containing water-soluble resin (E) | Material | — | — | Water-soluble resin PVA-2 | Water-soluble resin PVA-2 |
| | Thickness (μm) | — | — | 3.00 | 3.00 |
| Polylactic acid resin-containing layer (C) | Material | PLA-3 | PLA-3 | PLA-3 | PLA-3 |
| | Thickness (nm) | 500 | 500 | 150 | 150 |
| Evaluation result | Appearance | A | A | A | A |
| | Adherance | A | A | A | A |
| | Environmental load (Used amount of organic solvent) | A | A | A | A |
| | Workability of lamination | A | A | A | A |

TABLE 7

| | | Comparative Example 9 | Comparative Example 10 | Comparative Example 11 | Comparative Example 12 | Comparative Example 13 |
|---|---|---|---|---|---|---|
| Lamination method | | Dry lamination | Extrusion lamination | Heat lamination | Adhesive | Needle punching |
| Fibrous structure (B) containing water-soluble resin (A) | Material | Water-soluble resin PVA-1 | Water-soluble resin PVA-1 | Water-soluble resin PVA-1 | Water-soluble resin PVA-1 | Water-soluble resin PVA-1 |
| | Thickness (μm) | 300 | 300 | 300 | 300 | 300 |
| | Areal weight (g/m²) | 30 | 30 | 30 | 30 | 30 |

TABLE 7-continued

|  |  | Comparative Example 9 | Comparative Example 10 | Comparative Example 11 | Comparative Example 12 | Comparative Example 13 |
|---|---|---|---|---|---|---|
| Layer (D) containing water-soluble resin (E) | Material | — | — | — | — | — |
|  | Thickness (μm) | — | — | — | — | — |
| Polylactic acid resin-containing layer (C) | Material | PLA-1 | PLA-1 | PLA-1 | PLA-1 | PLA-1 |
|  | Thickness (nm) | 500 | 500 | 500 | 500 | 500 |
| Evaluation result | Appearance | C | C | C | A | C |
|  | Adherance | A | B | B | B | C |
|  | Environmental load (Used amount of organic solvent) | B | A | A | A | A |
|  | Workability of lamination | B | C | C | A | A |

INDUSTRIAL APPLICABILITY

Our laminate is a laminate laminated with at least one polylactic acid resin-containing layer (C) on at least one surface of a fibrous structure (B) containing a water-soluble resin (A), it is flexible and excellent in followability, adherence and coatability relative to an adherend having a curved surface, further it exhibits excellent compatibility to organs such as skin and internal organs, and the fibrous structure (B) containing a water-soluble resin (A) can be easily removed from the polylactic acid resin-containing layer (C) by an aqueous solution, and therefore, it is optimal for use in materials for external use on the skin such as wound-dressing materials, adhesion-preventing materials, and skin care products.

Further, the production method for the laminate is optimal for production of products attempting high functionality by lamination of a fibrous structure and a polylactic acid resin-containing layer, for example, medical products such as surgical gowns, stupes and artificial skins, and hygiene products such as diapers, gauze and first-aid adhesive tapes.

The invention claimed is:

1. A laminate comprising:
a polylactic acid resin-containing layer (C) having a thickness of 10 nm - 500 nm formed as a single layer and consisting of a polylactic acid resin, and optionally, an impact resistance improving agent, an antioxidant, a weather resistance agent, a thermal stabilizer, a lubricant, a nucleating agent, an ultraviolet absorber, and/or a colorant;
a dissolvable fibrous structure (B) consisting of a water-soluble resin (A); and
at least one dissolvable layer (D) consisting essentially of a water-soluble resin (E) with a thickness of 0.01 μm - 15 μm located between said dissolvable fibrous structure (B) and said polylactic acid resin-containing layer (C),
wherein the at least one dissolvable layer (D) has been partially dissolved with an aqueous solution such that the dissolvable fibrous structure (B) is wet-welded to the at least one dissolvable layer (D).

2. The laminate according to claim 1, wherein a time required for 0.04 ml of water applied to one surface of said dissolvable fibrous structure (B) to reach an opposite surface of said dissolvable fibrous structure (B) is 10 second to 5 minutes.

3. The laminate according to claim 1, wherein said water-soluble resin (A) contains a polyvinyl alcohol and/or a pullulan.

4. The laminate according to claim 1, wherein an areal weight of said dissolvable fibrous structure (B) is 1 g/m$^2$ to 1,000 g/m$^2$.

5. The laminate according to claim 1, wherein a thickness of said dissolvable fibrous structure (B) is 0.1 μm to 5,000 μm.

6. The laminate according to claim 1, wherein said polylactic acid resin is poly-D-lactic acid in an amount of 4 mol % to 50 mol %.

7. The laminate according to claim 1, wherein said polylactic acid resin has a weight average molecular weight of 30,000 or more.

* * * * *